US010456078B2

(12) United States Patent
Jayaraman et al.

(10) Patent No.: US 10,456,078 B2
(45) Date of Patent: Oct. 29, 2019

(54) WEARABLE DEVICE AND SYSTEM FOR PREVENTATIVE HEALTH CARE FOR REPETITIVE STRAIN INJURIES

(71) Applicants: Chandrasekaran Jayaraman, Chicago, IL (US); Adam J. Burns, Urbana, IL (US)

(72) Inventors: Chandrasekaran Jayaraman, Chicago, IL (US); Adam J. Burns, Urbana, IL (US)

(73) Assignees: Chandrasekaran Jayaraman, Chicago, IL (US); Adam J. Burns, Urbana, IL (US)

(*) Notice: Subject to any disclaimer, the term of this patent is extended or adjusted under 35 U.S.C. 154(b) by 159 days.

(21) Appl. No.: 15/449,103

(22) Filed: Mar. 3, 2017

(65) Prior Publication Data

US 2017/0251972 A1    Sep. 7, 2017

Related U.S. Application Data

(60) Provisional application No. 62/303,057, filed on Mar. 3, 2016.

(51) Int. Cl.
*A61B 5/00* (2006.01)
*G09B 19/00* (2006.01)
*G06F 19/00* (2018.01)
*A61B 5/11* (2006.01)

(52) U.S. Cl.
CPC .......... *A61B 5/486* (2013.01); *A61B 5/0022* (2013.01); *A61B 5/1112* (2013.01); *A61B 5/1118* (2013.01); *A61B 5/1125* (2013.01); *A61B 5/6806* (2013.01); *A61B 5/742* (2013.01); *A61B 5/746* (2013.01); *G06F 19/3481* (2013.01); *G09B 19/003* (2013.01); *A61B 2505/07* (2013.01); *A61B 2505/09* (2013.01)

(58) Field of Classification Search
CPC ...................................... A61B 5/486
See application file for complete search history.

(56) References Cited

U.S. PATENT DOCUMENTS

| | | | |
|---|---|---|---|
| 6,760,009 B2* | 7/2004 | Omura ............ | G06F 3/011 345/156 |
| 8,944,977 B2* | 2/2015 | Foster ............ | A63B 21/023 482/127 |
| 8,961,185 B2* | 2/2015 | Bleich ............ | A61B 5/0456 434/247 |
| 9,943,268 B1* | 4/2018 | LaBorde ......... | G06F 19/00 |
| 2006/0136285 A1* | 6/2006 | Alvarez .......... | G06Q 10/08 705/7.29 |
| 2006/0233632 A1* | 10/2006 | Hayes ............ | A61G 3/06 414/546 |

(Continued)

*Primary Examiner* — Xuan M Thai
*Assistant Examiner* — Sadaruz Zaman
(74) *Attorney, Agent, or Firm* — Birch IP Law Group

(57) ABSTRACT

A wearable device including a sensor system for Manual Wheelchair Users (MWCUs) to provide an alert to the MWCUs when there is an increased risk of injury is provided. The wearable device includes sensors measuring the physical activity of the MWCU and transmitting it as user data to a user motion dynamics analysis system on a user device. When the user motion dynamics analysis system determines that there is a risk of injury, it transmits an alert to the wearable device for display to the user.

12 Claims, 19 Drawing Sheets

(56) References Cited

U.S. PATENT DOCUMENTS

| | | | |
|---|---|---|---|
| 2006/0281980 A1* | 12/2006 | Randlov | A61B 5/14532 |
| | | | 600/301 |
| 2006/0282021 A1* | 12/2006 | DeVaul | A61B 5/0024 |
| | | | 600/595 |
| 2008/0004550 A1* | 1/2008 | Einav | G06F 19/00 |
| | | | 601/33 |
| 2010/0157291 A1* | 6/2010 | Kiesel | G01N 15/1429 |
| | | | 356/244 |
| 2011/0270135 A1* | 11/2011 | Dooley | A61B 5/1121 |
| | | | 600/595 |
| 2013/0006718 A1* | 1/2013 | Nielsen | G06Q 10/06312 |
| | | | 705/7.42 |
| 2013/0046438 A1* | 2/2013 | Summer | A61G 5/10 |
| | | | 701/36 |
| 2013/0218456 A1* | 8/2013 | Zelek | G01C 21/3652 |
| | | | 701/412 |
| 2016/0143593 A1* | 5/2016 | Fu | A61B 5/7264 |
| | | | 600/595 |
| 2017/0095382 A1* | 4/2017 | Wen | G06F 19/3418 |
| 2017/0251972 A1* | 9/2017 | Jayaraman | A61B 5/6806 |
| 2018/0040258 A1* | 2/2018 | Kouache | G01C 21/3652 |
| 2018/0225421 A1* | 8/2018 | Balasubramanian | G16H 50/30 |

* cited by examiner

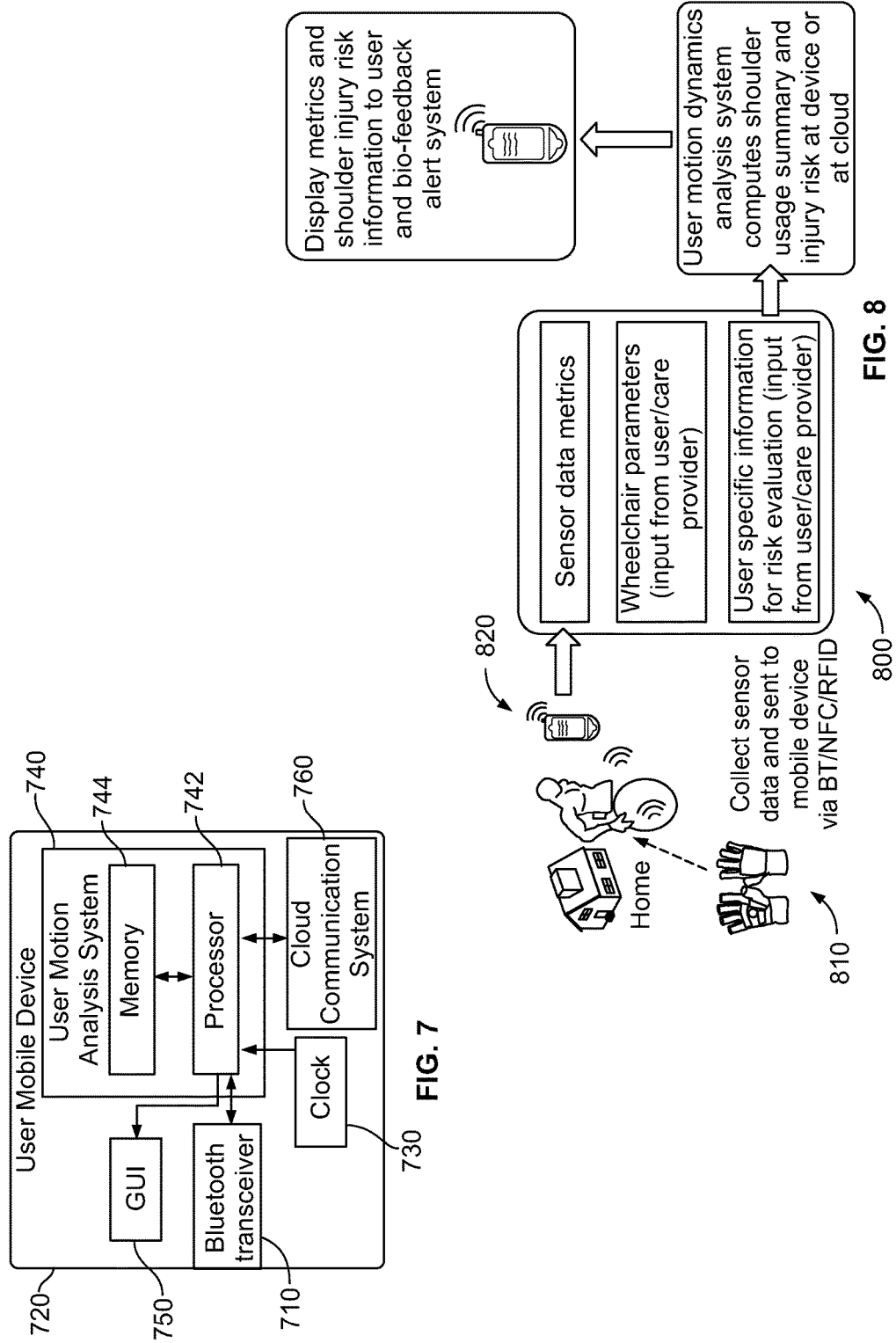

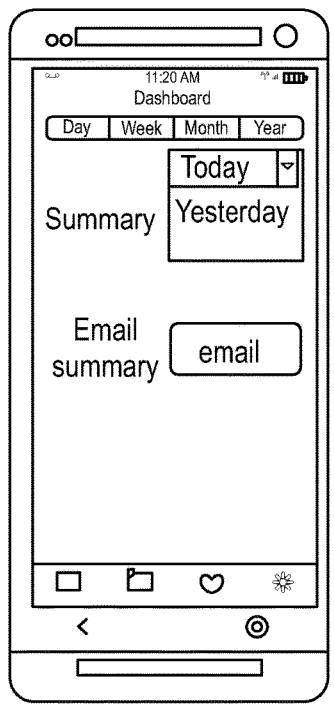 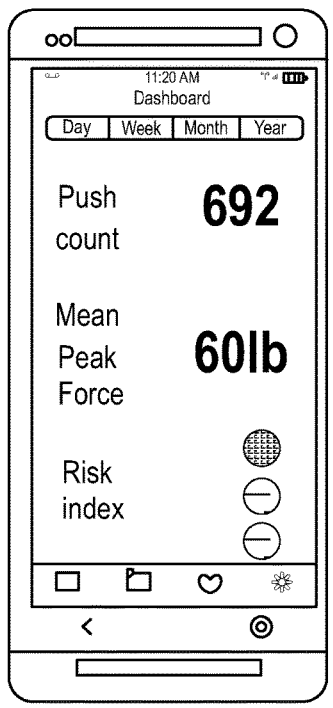 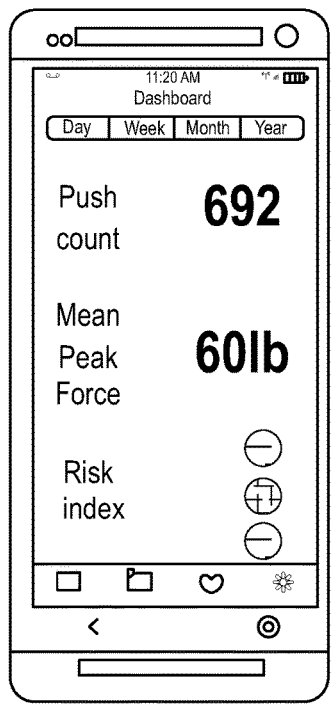
FIG. 11A  FIG. 11B  FIG. 11C
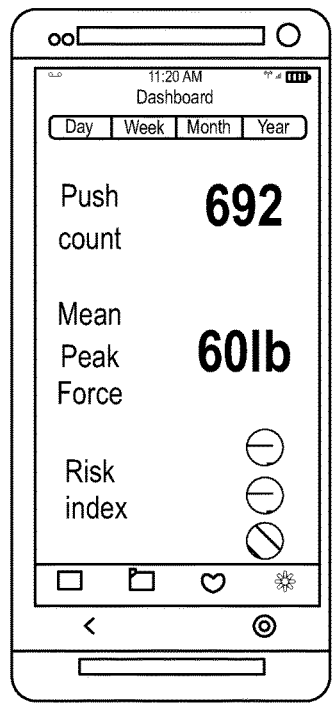 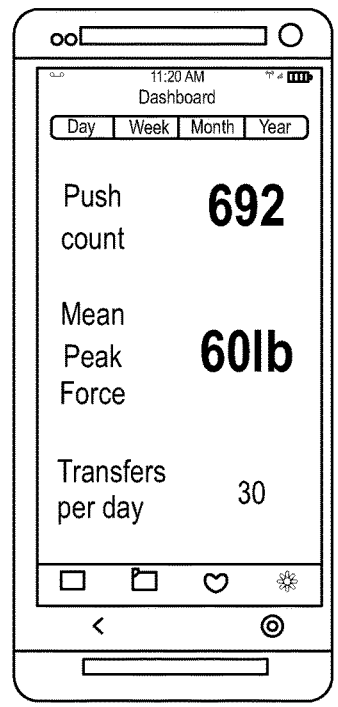
FIG. 11D  FIG. 11E $U1_{weight}$

| BMI ranges | Criteria | Rating | Weightages |
|---|---|---|---|
| Normal | BMI<25 | 1 | 1.2 |
| Overweight | 25<BMI<30 | 2 | 3 |
| Obese | BMI>30 | 3 | 6 |

$U2_{weight}$

| Wheelchair Weight | Criteria | Rating | Weightages |
|---|---|---|---|
| Ultra Light weight | Weight<30 lb | 1 | 1 |
| Light Weight | 30.1 lb<weight<34 lb | 2 | 2 |
| Standard | 34.1 lb<weight<36 lb | 3 | 3 |
| Heavy duty | 36.1 lb< weight<60 lb | 4 | 6 |

Note: In general if body weight> 250 lb, a heavy duty wheelchair is recommended.

$U3_{weight}$
Wheelchair Configuration

| Wheelchair Configuration | Criteria | Rating | Weightages |
|---|---|---|---|
| | Optimal | 1 | 1 |
| | Near optimal(but slightly deviates (within 10%)) | 2 | 3 |
| | Large deviation than optimal (greater than 10%) | 4 | 6 |

Optimal wheelchair configuration is decided based on shoulder position with respect to the wheel axle and shoulder angles during push. These are obtained from sensors.

$U4_{weight}$
Age of Injury/causes leading to wheelchair use

| Age of Injury/causes leading to wheelchair use | Criteria | Rating | Weightages |
|---|---|---|---|
| Congenial | Birth | 1 | 1 |
| Young | Age up to 20 | 2 | 2 |
| Young adult | 20<Age<30 | 3 | 3 |
| Other | Age>30 yrs | 4 | 6 |

$U5_{weight}$

| Gender | Risk Scores | Weightages |
|---|---|---|
| Male | 1.1 | 1 |
| Female | 2 | 3 |

FIG. 14A

$U6_{weight}$

| Time since injury | Criteria | Rating | Weightages |
|---|---|---|---|
| | 1 month <Time <12 months | 1 | 1 |
| | 12 months <Time < 24 months | 2 | 2 |
| | 24 months <Time < 48 months | 3 | 3 |
| | 48 months <Time | 4 | 6 |

User demographics specific risk exposure score:

U index= $(1/C1^* (U1_{weight})) \times (1/C2^* (U2_{weight})) \times (1/C3^* (U3_{weight})) \times (1/C4^* (U4_{weight})) \times (1/C5^* (U5_{weight})) \times (1/C6^* (U6_{weight}))$ Where the Ci's are the number of factors included.

FIG. 14B

Self reported scores
Shoulder, elbow or wrist pain scales/index

$S1_{wrist\ weight}$

| Self perceived pain | Criteria | Rating | Weightages |
|---|---|---|---|
| Wrist | No | 0 | 1 |
| | Light | 1 to 1.9 | 1.1 |
| | Somewhat paining | 2 to 3.9 | 3 |
| | Pain | 4 to 5.9 | 6 |
| | Very painful (but can use hands) | 6 to 7.9 | 9 |
| | Unbearable Pain(cannot use hand) | 8 to 10 | 13 |

$S1_{elbow\ weight}$

| Self perceived pain | Criteria | Rating | Weightages |
|---|---|---|---|
| Elbow | No | 0 | 1 |
| | Light | 1 to 1.9 | 1.1 |
| | Somewhat paining | 2 to 3.9 | 3 |
| | Pain | 4 to 5.9 | 6 |
| | Very painful (but can use hands) | 6 to 7.9 | 9 |
| | Unbearable Pain(cannot use hand) | 8 to 10 | 13 |

$S1_{Shoulder\ weight}$

| Self perceived pain | Criteria | Rating | Weightages |
|---|---|---|---|
| Shoulder | No | 0 | 1 |
| | Light | 1 to 1.9 | 1.1 |
| | Somewhat paining | 2 to 3.9 | 3 |
| | Pain | 4 to 5.9 | 6 |
| | Very painful (but can use hands) | 6 to 7.9 | 9 |
| | Unbearable Pain(cannot use hand) | 8 to 10 | 13 |

User perceived pain exposure score:
Perceived pain index : $S1_{wrist\ weight} \times S1_{elbow\ weight} \times S1_{Shoulder\ weight}$
Where the Si's are the number of factors included.

FIG. 15

$S2_{weight}$

| Self reported quality of living (QOL) | Criteria | Rating | Weightages |
|---|---|---|---|
| | Good | 1 | 1 |
| | Little difficult (once or twice) | 2 | 1.5 |
| | Much difficult (sometimes) | 3 | 2 |
| | Severely difficult (often) | 4 | 3 |

$S3_{weight}$

| Self reported activity of daily living (ADL) | Criteria | Rating | Weightages |
|---|---|---|---|
| | Good | 1 | 1 |
| | Little difficult (once or twice) | 2 | 1.5 |
| | Much difficult (sometimes) | 3 | 2 |
| | Severely difficult (often) | 4 | 3 |

$S4_{weight}$

| Self reported independent activity of daily living (IADL) | Criteria | Rating | Weightages |
|---|---|---|---|
| | Live independently | 1 | 1 |
| | Little difficult (help needed once or twice) | 2 | 1.5 |
| | Much difficult (needs help to live independently) | 3 | 2 |
| | Severely difficult (can't live independently) | 4 | 3 |

User perceived quality of life score:
Perceived QOL : $S2_{weight}$ X $S3_{weight}$ X $S4_{weight}$
$S5_{weight}$
Weightage/scores based on other inputs from healthcare providers consolidated as appropriate scores for risk (MRi, ultrasonic, AISA,B,C
$S6_{weight}$
Severity of injury (AIS etc scores and convert it to scale score)

S index$_{wrist}$ = ($S1_{wrist\ weight}$) X ($S2_{weight}$) X ($S3_{weight}$) X ($S4_{weight}$) X ($S5_{weight}$) X ($S6_{weight}$)

S index$_{elbow}$ = ($S1_{elbow\ weight}$) X ($S2_{weight}$) X ($S3_{weight}$) X ($S4_{weight}$) X ($S5_{weight}$) X ($S6_{weight}$)

S index$_{shoulder}$ = ($S1_{shoulder\ weight}$) X ($S2_{weight}$) X ($S3_{weight}$) X ($S4_{weight}$) X ($S5_{weight}$) X ($S6_{weight}$)

Where the Si's are the number of factors included.

FIG. 16

Wheelchair propulsion
$W1_{weight}$

| Pattern type | Criteria | Rating | Weightages |
|---|---|---|---|
| | SC | 1 | 1.1 |
| | DLOP | 2 | 1.5 |
| | SLOP | 3 | 2 |
| | ARC | 4 | 3 |

$W2_{weight}$

| Mean speed | Criteria | Rating | Weightages |
|---|---|---|---|
| Very slow | Speed<0.7 self pace speed | 1 | 1.1 |
| Slow | 0.8 self pace< speed< self pace speed | 2 | 1.2 |
| Self pace | Self pace speed | 3 | 1 |
| Fast | 1.3 self pace> speed> self pace speed | 4 | 1.5 |
| Very fast | Speed> 1.3 self pace speed | 5 | 2 |

$W3_{wrist\ weight}$
Intensity of average peak resultant force per push/per arm (% of BMI?)

| Intensity of average peak resultant force per push at wrist | Rating | Weightages |
|---|---|---|
| Light | 1 | 1 |
| Somewhat hard | 2 | 3 |
| Hard | 3 | 6 |
| Very hard | 4 | 9 |
| Near Maximal | 5 | 13 |

$W4_{weight}$

| Number of pushes per minute (Efforts/min) | Criteria | Rating | Weightages |
|---|---|---|---|
| Light | <4 | 1 | 0.5 |
| Somewhat hard | 4-8 | 2 | 1.0 |
| Hard | 9-14 | 3 | 1.5 |
| Very hard | 15-19 | 4 | 2 |
| Near Maximal | >19 | 5 | 3 |

FIG. 17A

$W5_{weight}$

| Trunk posture while propulsion | Criteria | Rating | Weightages |
|---|---|---|---|
| Very good | Optimal value | 1 | 1.0 |
| Good | Optimal value± 5% | 2 | 1.0 |
| Fair | 1.05* optimal value<posture<1.1* optimal value | 3 | 1.5 |
| Bad | 1.1* optimal value<posture<1.5* optimal value | 4 | 2 |
| Very bad | 1.5* optimal value<posture | 5 | 3 |

Optimal trunk posture criteria established using metric from sensors placed in upper body.

$W6_{weight}$

| Duration of push/ day | Criteria (minutes) | Rating | Weightages |
|---|---|---|---|
| | <20 min | 1 | 1.0 |
| | 20<duration<40 | 2 | 1.0 |
| | 40<duration<60 | 3 | 1.5 |
| | 60<duration<90 | 4 | 2 |
| | 90<duration | 5 | 3 |

$W7_{weight}$

| Duration of recovery/ day | Criteria (minutes) | Rating | Weightages |
|---|---|---|---|
| | <20 min | 1 | 1.0 |
| | 20<duration<40 | 2 | 1.0 |
| | 40<duration<60 | 3 | 1.5 |
| | 60<duration<90 | 4 | 2 |
| | 90<duration | 5 | 3 |

$W8_{weight}$

| Duration of total propulsion/ day (add above 2) | Criteria (minutes) | Rating | Weightages |
|---|---|---|---|
| | <40 min | 1 | 1.0 |
| | 40<duration<80 | 2 | 1.0 |
| | 80<duration<120 | 3 | 1.5 |
| | 120<duration<180 | 4 | 2 |
| | 180<duration | 5 | 3 |

FIG. 17B

$W9_{weight}$

| Push time to recovery time ratio | This will also give total push activity time per day | Rating | Weightages |
|---|---|---|---|
| | Ratio>1 | 5 | 3 |
| | 0.9≤Ratio≤1 | 4 | 2 |
| | 0.75≤Ratio<0.9 | 3 | 1.5 |
| | 0.5≤Ratio<0.75 | 2 | 1 |
| | Ratio<0.5 | 1 | 1 |

$W10_{weight}$

| Momentary impact endured by arm joint | Criteria | Rating | Weightages |
|---|---|---|---|
| | Light | 1 | 1.0 |
| | Somewhat impactful | 2 | 1.1 |
| | Impactful | 3 | 1.5 |
| | Very impactful | 4 | 2 |
| | Near Maximal | 5 | 3 |

Note: Jerk during propulsion and recovery and jerk during transfer and bouts can be extracted from acceleration data at wrist and inertia sensor at wheelchair.

$W11_{weight}$

| Wheelchair pushed in level or incline (uphill/downhill) | Rating | Weightages |
|---|---|---|
| Level ground (0 deg) | 1 | 0.5 |
| 0 to 2 deg | 2 | 1.0 |
| 2 to 4 deg | 3 | 1.5 |
| 4 to 6 deg | 4 | 2 |
| Greater than 6 deg | 5 | 3 |

$W12_{weight}$

| Tire pressure | Rating | Weightages |
|---|---|---|
| Optimal | 1 | 1 |
| Differs from optimal | 2 | 3 |

$W13_{weight}$

| Contact angle | Criteria | Rating | Weightages |
|---|---|---|---|
| Very good | Optimal | 1 | 1.0 |
| Good | Optimal ± 5% | 2 | 1.0 |
| Fair | 1.05* optimal value< contact angle<1.1* optimal value | 3 | 1.5 |
| Bad | 1.1* optimal value< contact angle<1.5* optimal value | 4 | 2 |
| Very bad | 1.5*optimal value< contact angle | 5 | 3 |

* Optimal determined with configuration and day-to-day use from device sensor data

FIG. 17C

$$W\ index_{hand} = (W1_{weight}) \times (W2_{weight}) \times (W3_{wrist\ weight}) \times (W4_{weight})$$
$$\times (W5_{weight}) \times (W6_{weight}) \times (W7_{weight}) \times (W8_{weight}) \times (W9_{weight})$$
$$\times (W10_{weight}) \times (W11_{weight}) \times (W12_{weight}) \times (W13_{weight})$$

Where the Wi's are the number of factors included.

Inverse dynamics

| Intensity of average peak resultant force per push at elbow | Rating | Weightages |
|---|---|---|
| Light | 1 | 1 |
| Somewhat hard | 2 | 3 |
| Hard | 3 | 6 |
| Very hard | 4 | 9 |
| Near Maximal | 5 | 13 |

$$W\ index_{elbow} = (W1_{weight}) \times (W2_{weight}) \times (W3_{elbow\ weight}) \times (W4_{weight})$$
$$\times (W5_{weight}) \times (W6_{weight}) \times (W7_{weight}) \times (W8_{weight}) \times (W9_{weight})$$
$$\times (W10_{weight}) \times (W11_{weight}) \times (W12_{weight})$$

Where the Wi's are the number of factors included.

| Intensity of average peak resultant force per push at shoulder | Rating | Weightages |
|---|---|---|
| Light | 1 | 1 |
| Somewhat hard | 2 | 3 |
| Hard | 3 | 6 |
| Very hard | 4 | 9 |
| Near Maximal | 5 | 13 |

$$W\ index_{Shoulder} = (W1_{weight}) \times (W2_{weight}) \times (W3_{shoulder\ weight}) \times (W4_{weight})$$
$$\times (W5_{weight}) \times (W6_{weight}) \times (W7_{weight}) \times (W8_{weight}) \times (W9_{weight})$$
$$\times (W10_{weight}) \times (W11_{weight}) \times (W12_{weight})$$

Where the Wi's are the number of factors included.

FIG. 17D

Transfer

$T1_{weight}$

| Number of transfers/day (Efforts/day) | Criteria | Rating | Weightages |
|---|---|---|---|
| Light | <4 | 1 | 0.5 |
| Somewhat hard | 4-8 | 2 | 1.0 |
| Hard | 9-14 | 3 | 1.5 |
| Very hard | 15-19 | 4 | 2 |
| Near Maximal | >19 | 5 | 3 |

$T2_{weight}$

| Trunk posture while transfer | Criteria | Rating | Weightages |
|---|---|---|---|
| Very good | Optimal value | 1 | 1.0 |
| Good | Optimal value± 5% | 2 | 1.0 |
| Fair | 1.05* optimal value<posture<1.1* optimal value | 3 | 1.5 |
| Bad | 1.1* optimal value<posture<1.5* optimal value | 4 | 2 |
| Very bad | 1.5* optimal value<posture | 5 | 3 |

Optimal trunk posture criteria established using metric from sensors placed in upper body.

$T3_{wrist\ weight}$

| Intensity of average peak resultant force per transfer at wrist | Rating | Weightages |
|---|---|---|
| Light | 1 | 1 |
| Somewhat hard | 2 | 3 |
| Hard | 3 | 6 |
| Very hard | 4 | 9 |
| Near Maximal | 5 | 13 |

$T3_{elbow\ weight}$

| Intensity of average peak resultant force per transfer at wrist | Rating | Weightages |
|---|---|---|
| Light | 1 | 1 |
| Somewhat hard | 2 | 3 |
| Hard | 3 | 6 |
| Very hard | 4 | 9 |
| Near Maximal | 5 | 13 |

FIG. 18A

$T3_{shoulder\ weight}$

| Intensity of average peak resultant force per transfer at wrist | Rating | Weightages |
|---|---|---|
| Light | 1 | 1 |
| Somewhat hard | 2 | 3 |
| Hard | 3 | 6 |
| Very hard | 4 | 9 |
| Near Maximal | 5 | 13 |

$T4_{weight}$

| Momentary impact endured by arm joint while transferring | Criteria | Rating | Weightages |
|---|---|---|---|
| | Optimal value | 1 | 1.0 |
| | Optimal value ± 5% | 2 | 1.0 |
| | 1.05* optimal value<impact<1.1* optimal value | 3 | 1.5 |
| | 1.1* optimal value<impact<1.5* optimal value | 4 | 2 |
| | 1.5* optimal value<impact | 5 | 3 |

T index $_{wrist}$ = (T1$_{weight}$) X (T2$_{weight}$) X (T3$_{wrist\ weight}$) X (T4$_{weight}$)

T index $_{elbow}$ = (T1$_{weight}$) X (T2$_{weight}$) X (T3$_{elbow\ weight}$) X (T4$_{weight}$)

T index $_{shoulder}$ = (T1$_{weight}$) X (T2$_{weight}$) X (T3$_{shoulder\ weight}$) X (T4$_{weight}$)

Where the Ti's are the number of factors included.

FIG. 18B

WEARABLE DEVICE AND SYSTEM FOR PREVENTATIVE HEALTH CARE FOR REPETITIVE STRAIN INJURIES

CROSS-REFERENCE TO RELATED APPLICATIONS

The present application claims the benefit of U.S. Provisional Application No. 62/303,057 filed Mar. 3, 2016, entitled "Cloud Based Preventative Healthcare Wearable Device and System for Repetitive Strain Injuries", which is hereby incorporated by reference in its entirety.

BACKGROUND OF THE INVENTION

The present invention generally relates to healthcare monitoring devices. More particularly, the present invention relates to a wearable, network connected healthcare monitoring system for monitoring injury or activity.

Repetitive tasks that are performed in many aspects of daily life may lead to strain and/or stress injuries. Such injuries frequently occur in a population such as individuals using assistive devices such as walkers, wheelchairs for example, and/or individuals engaged in occupational situations such as repeated load carriage, repeated gripping tasks, etc.

One example of an assistive device in which requires repeated physical effort on the part of a user is a wheelchair that is manually operated. Such wheelchair users must effectively learn to walk with their hands. Over 3 million manual wheelchair users (MWCUs) in the U.S. face this reality every day. Research shows that about 70% of MWCUs (approximately 2.1 million in U.S. alone) experience debilitating shoulder injuries within the first 12 months of using a manual wheelchair due to repetitive propulsion. Shoulder pain in MWCUs negatively impacts their quality and independence of living. Moreover, this pain increases their disability and health care costs.

Studies have shown that clinical training of MWCUs on proper propulsion technique and providing continuous feedback on their propulsion technique reduces the risk of shoulder injury. However such training is not widely accessible to MWCU and clinicians.

FIG. 1 illustrates the current status of such propulsion technique training. As shown in FIG. 1, today the MWCU must leave their home and travel to a clinical and/or research facility. At the facility, the MWCU demonstrates their usage of the wheelchair for a clinician and the clinician evaluates their usage of the wheelchair. This evaluation typically required the MWCU is use a specialized device or equipment with force sensing instrumented wheels. Such equipment typically costs in excess of U.S. $40,000. Additionally, MWCU access to the facility may be constrained because there are only a limited number of available professionals with the capacity to provide such analysis and training. Also, MWCUs face various barriers such as arranging transportation and the cost of transportation that may reduce their ability to visit specialized clinics to receive training. Consequently, many MWCUs do not receive this analysis and training, or may not receive it in a timely manner. This in turn exposes the MWCUs to higher injury risk and higher health care costs, especially due to the cost of having to treat additional stress and/or strain injuries that might arise.

Additionally, such clinical training may not capture the daily reality of the MWCU's physical activity because the clinical evaluation is an artificial situation wherein the MWCU knows that their physical activity is being evaluated and consequently is seeking to emulate the most proper technique for the clinician. Consequently, the clinician's ability to analyze and give feedback with regard to the MWCU's typically technique may be limited. Additionally, the clinical evaluation typically lasts for only a finite amount of time and consequently may not allow the clinician an opportunity to accurately evaluate the physical motion of the MWCU when the MWCU is fatigued and may be more susceptible to injury.

BRIEF SUMMARY OF THE INVENTION

One or more of the embodiments of the present invention provide a wearable device including a sensor system for Manual Wheelchair Users (MWCUs) and a feedback system wherein said sensor system senses user sensor data and transmits it to a user motion dynamics analysis system on a user mobile device. The user sensor data is used along with stored information including customized desired propulsion metrics by the user motion dynamics analysis system to determine a risk prediction for an injury. When the user motion dynamics analysis system determines that there is a risk of injury, an alert instruction is transmitted from the user device to the wearable device and cause the actuation of feedback system in the wearable device that is observable by the user. Although in one embodiment, the invention may be used for a MWCUs, other embodiments may be employed for other applications such as training and tracking for assistive devices such as walkers, crutches, etc and training and tracking of any gripping task.

BRIEF DESCRIPTION OF THE DRAWINGS

FIG. 7 illustrates an embodiment of the user mobile device.

FIG. 8 illustrates the data process flow of the wearable user motion dynamics analysis system of FIG. 2.

FIGS. 11A-11E illustrate various embodiments of the report display interfaces.

FIGS. 14A and 14B illustrate an example of the calculation of the user demographics specific risk exposure score.

FIG. 15 illustrates an example of the calculation of the user perceived pain exposure score.

FIG. 16 illustrates an example of the calculation of the user perceived quality of life score.

FIGS. 17A to 17D illustrate an example of the calculation of the wheelchair propulsion score.

FIGS. 18A and 18B illustrate an example of the calculation of the transfer score.

DETAILED DESCRIPTION OF THE INVENTION

Figure 1:
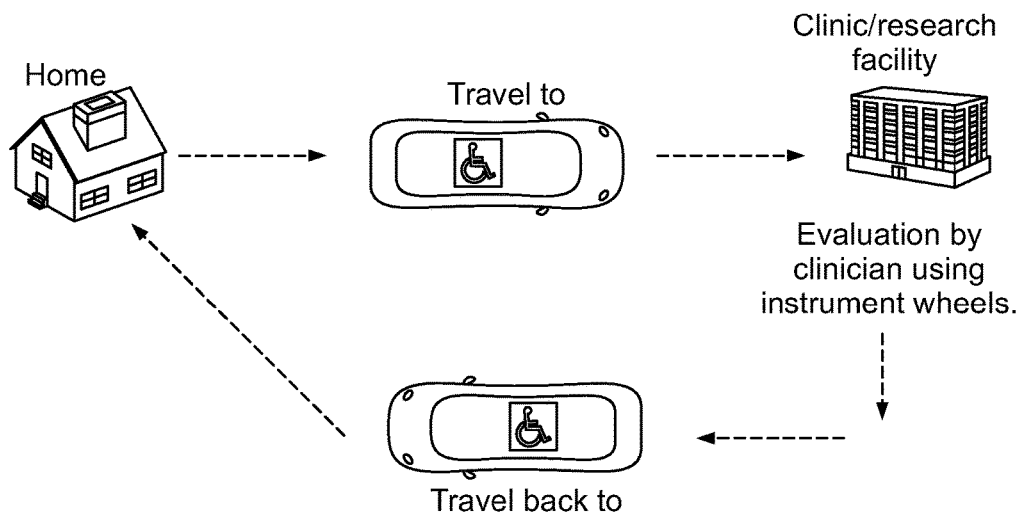
FIG. 1 illustrates the current status of Manual Wheelchair User (MWCU) propulsion technique training.

Various remote monitoring healthcare systems exist today. Integration with remote patient information, historical data, and detailed individual bioinformatic data may increase awareness in the user, as well as provide a desirable component to the healthcare system provided by clinicians. Analysis of patient data may be supplemented with remotely acquired data. The facilitation of providing training materials recommended by the healthcare provider may lead to a reduced risk of patient injury through early warning detection. Patients benefit from remote systems through the reduction in required transportation, time spent at clinics, and money spent on insurance copays.

To address the problems mentioned above, which are of significant public health importance, one or more embodiments of the present invention provide a local and/or a cloud-integrated wearable technology that improves the quality of life and/or efficacy of MWCUs by providing easier access (home-based access as opposed to clinical access) to wheelchair propulsion training and performance feedback, including an injury-risk information derived from learning sensor data. All these are provided using a mobile device. Using the cloud-integrated functionality, individuals may share their performance data with their healthcare providers, family, trainers, and/or coach. The healthcare providers, family members, trainers, and/or coach may monitor their client's performance from a remote location and provide customized feedback, training, and/or alert recommendations. The system may continuously track the arm usage and may acts as a decision support system to for preventive healthcare as further discussed below.

Currently, for home based rehabilitation training and/or monitoring such as for wheelchair users, there exists no way to remotely send and receive training information gathered from wearable devices along with healthcare-provided customized training feedback based on extracted information from sensor data. No current glove embedded wearable technologies for manual wheelchair users use sensor data from wearable device information in predicting injury risk by providing a risk-predicting assessment to help prevent and delay the onset of upper appendage repetitive stress and/or strain injuries.

As further described below, one or more embodiments of the present invention provide a local and/or cloud-based wearable technology that reduces the risk of shoulder injury in MWCUs by providing access to affordable home-based propulsion/rehabilitation training and feedback. One embodiment of the present invention provides a pair of gloves with embedded sensors, including, but not limited to, force sensors and acceleration sensors and gyroscopes, capable of accurately measuring and securely transmitting real-time sensor data to a mobile phone application, pc application, or tablet application. While a user is propelling his/her wheelchair wearing the gloves, sensor data from the gloves is collected and automatically sent wirelessly to the user motion and force analysis system on the user's mobile device, computer, or tablet. Based on the received sensor data, the user motion and force analysis system also estimates customized injury-risk information, and provides bio-feedback to the user on their day-to-day assistive device use/push pattern in order to help maintain proper propulsion technique. The bio-feedback includes, but is not limited to, display of summary information on the users mobile device screen, sensory feedback (auditory/vibratory), text/voice/video data exchange and email notification. The bio-feedback may be a closed loop, wherein the user may receive, share and/or send the information using the cloud for efficient healthcare. The wheelchair propulsion and injury risk metrics are computed using measurements from the sensor data, including the number of pushes, accelerometry (movement), inertial measurements (movement and orientation), push time, activity rate, and peak force during different activities of daily living in manual wheelchair users.

Figure 2:
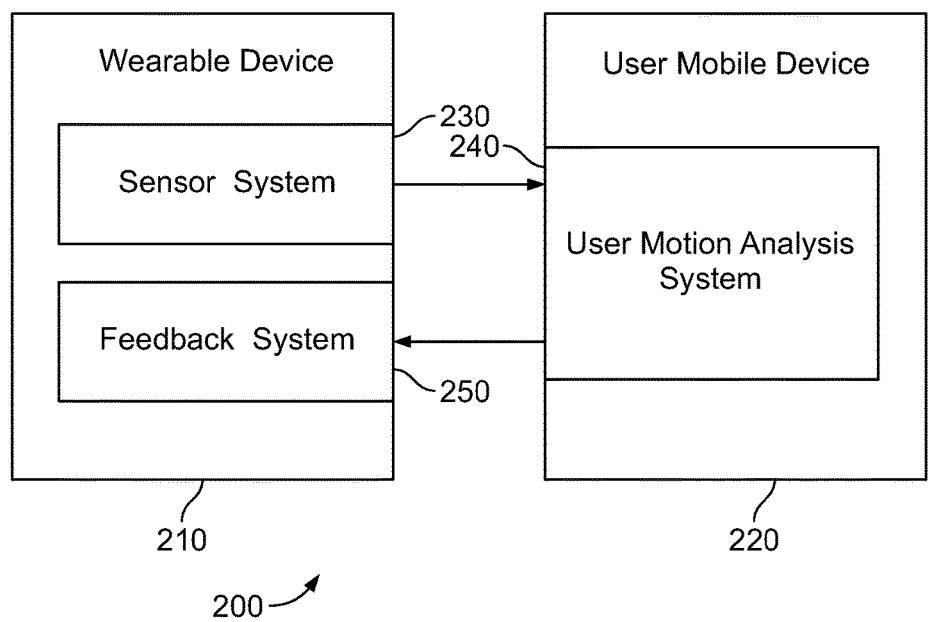
FIG. 2 illustrates a simplified version of a wearable user motion dynamics analysis system according to an embodiment of the present invention.

FIG. 2 illustrates a simplified version of a wearable user motion dynamics analysis system 200 according to an embodiment of the present invention. As shown in FIG. 2, the user motion dynamics analysis system 200 includes a wearable device 210 having sensor system 230 and a feedback system 250 and a user mobile device 220 including a user motion dynamics analysis system 240.

In operation, the wearable device 210 may be positioned on a user and the sensor system 230 may detect the motion and grip force of the user during wheelchair use and relay it as user motion and force data to the user motion dynamics analysis system 240 at the user mobile device 220. The user mobile device 220 may for example be any of a smartphone or mobile phone, computer, smart watch, or tablet device.

As further described below, the user motion dynamics analysis system 240 uses a complex computerized technique to analyze the received user motion and force data and detect when the user motion and force data departs from a predetermined and/or dynamically determined desired set of parameters. If such a deviation is detected, the user motion dynamics analysis system 240 transmits alert data to the feedback system 250. In response, the feedback system 250 may display an alert and/or alarm to the user to that the user will be aware that their motion and force deviates from desired parameters. Preferably, the user will then adjust their motion and force to conform with desired parameters in order to reduce the risk of injury.

Figure 3:
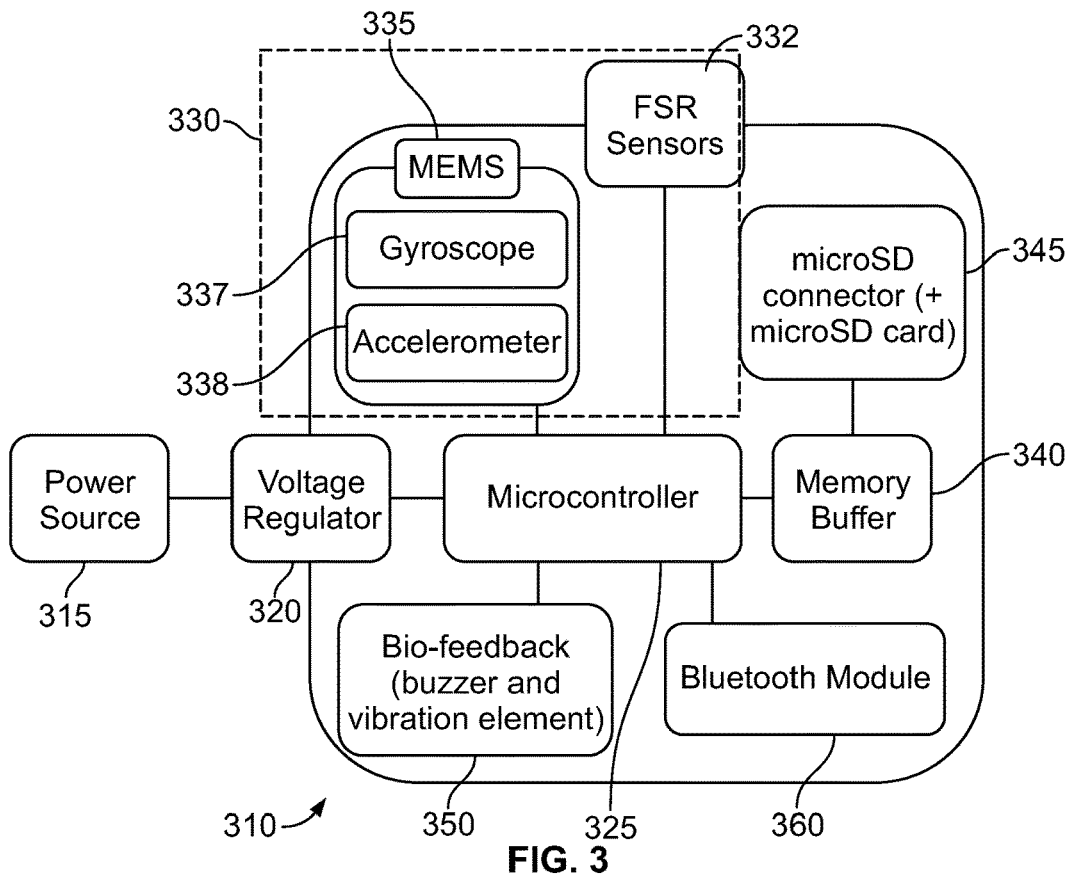
FIG. 3 illustrates a first embodiment of a wearable device as discussed in FIG. 2.

FIG. 3 illustrates a first embodiment of a wearable device 310 as discussed in FIG. 2. As shown in FIG. 3, the wearable device 310 includes a power source 315, a voltage regulator 320, a microcontroller 325, a user sensor system 330, a memory buffer 340, an memory system 345 such as a microSD card and associated connector, a feedback system 350 such as a biofeedback buzzer and/or vibration element, and a Bluetooth module 360, such as a Bluetooth Low Energy module. The user sensor system 330 includes one or more force sensing resistors 332 and Microelectromechanical systems (MEMS) 335 that include a gyroscope 337 and accelerometer 338.

In operation, power is supplied to the wearable device 310 by the power source 315 and regulated by the voltage regulator 320. The user sensor system 330 detects user data from the force sensing resistors 332, gyroscope 337, and accelerometer 338. The user data is then passed to the microcontroller 325. The microcontroller 325 directs the user data into the memory buffer 340 where it is buffered while being written to the memory system 345. Additionally, the microcontroller 325 may cause the user data to be passed to the Bluetooth module 360 for communication to the user motion dynamics analysis system 240 of the user mobile device 220 as shown in FIG. 2.

As mentioned in FIG. 2, if the user motion dynamics analysis system 240 determines that the user data departs from the predetermined and/or dynamically determined desired set of parameters, the user motion dynamics analysis system 240 transmits alert data. The alert data is received by the Bluetooth module 360 and relayed to the microcontroller 325. The microcontroller 325 received the alert data and activates the feedback system 350 in response to the alert data.

As further discussed below, the feedback system 350 may provide several alert options. For example, the feedback system 350 may include a vibration element and the vibration element may be optionally controlled to any of several available levels of vibration. In this embodiment, the alert data may specify the level of vibration to be delivered by the feedback system 350. Similarly, when the feedback system 350 includes an audible component such as a buzzer, the alert data may specify the volume of the audible component. Additionally, when the feedback system 350 includes multiple display elements such as a buzzer and a vibration element, the alert data may specify which of the display elements is to be activated by the microcontroller 325, including optional activation of one or the other of the display elements and/or simultaneous display of more than one of the display elements.

In one embodiment, all of the components of the wearable device other than the power source may be located on a single Printed Circuit Board (PCB).

In one embodiment, an ARM microcontroller is used. Communication with a micro SD card module, in the form of a component of the PCB, is managed by the microcontroller using an SPI bus. Sensor data is received and converted using an on-chip analog to digital converter. The sensor data is saved directly onto the microSD card, as well as transmitted wirelessly, using a separate low power Bluetooth module that communicates using the SPI protocol. One specific embodiment of this design utilizes an ARM ATMEGA328p-au microcontroller, an EEPROM memory buffer, an nRF8001 low-power Bluetooth IC module capable of wirelessly sending and receiving data, and JST-XH connectors to attach and detach force-sensitive resistors and power sources.

Recharging of the power source 315 such as a battery is accomplished using a mini USB connector and a standard battery management charge controller such as a Microchip MCP73831T. This provides a system for charging the device at any time, including during operation by the user. In various embodiments where an on-board storage device is employed, a real time clock is included on the PCB along with a backup coin cell battery in order to maintain accurate timestamp readings for data logging purposes.

Figure 4:
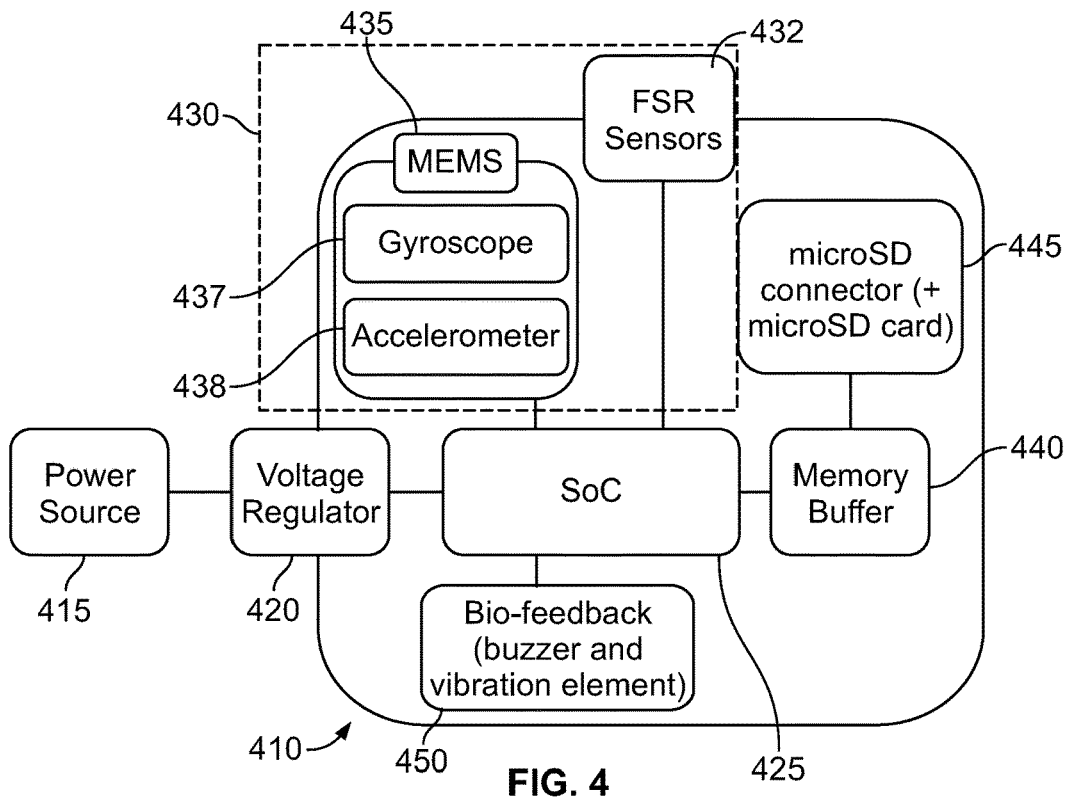
FIG. 4 illustrates a second embodiment of a wearable device as discussed in FIG. 2.

FIG. 4 illustrates a second embodiment of a wearable device 410 as discussed in FIG. 2. Similar to the embodiment shown in FIG. 3, as shown in FIG. 4, the wearable device 410 includes a power source 415, a voltage regulator 420, a System On a Chip (SoC) 425, a user sensor system 430, a memory buffer 440, an memory system 445 such as a microSD card and associated connector, and a feedback system 450 such as a biofeedback buzzer and/or vibration element. The user sensor system 430 includes one or more force sensing resistors 432 and Microelectromechanical systems (MEMS) 435 that include a gyroscope 437 and accelerometer 438.

In operation, the wearable device 410 of FIG. 4 operates similarly to the wearable device 310 of FIG. 3, but employs the SoC 425 instead of the microcontroller 325 and Bluetooth module 360 of FIG. 3. The SoC 425 includes a processor that operates similarly to the microcontroller 325 of FIG. 3 and a wireless communication system such as a Bluetooth 4.0 transceiver that operates similarly to the Bluetooth module 360 of FIG. 3 as described above.

In one embodiment, a low-power SoC microcontroller unit is used for the main processing module in the PCB. A built-in analog to digital converter of the SoC processes the sensor data from the device. Wireless communication with a mobile device, tablet, computer or other such device is achieved using the Bluetooth 4.0 transceiver, which is built into the SoC. In one embodiment, the SoC is a Nordic nRF51422. In a separate embodiment, the SoC is a Dialog Semiconductor NRF51422. In yet another embodiment, the SoC is a NXP Semiconductors QN902X. In one or more of the embodiments described above, I2C and SPI busses are used to communicate with on-board peripherals, including the micro SD card module.

Figure 5:
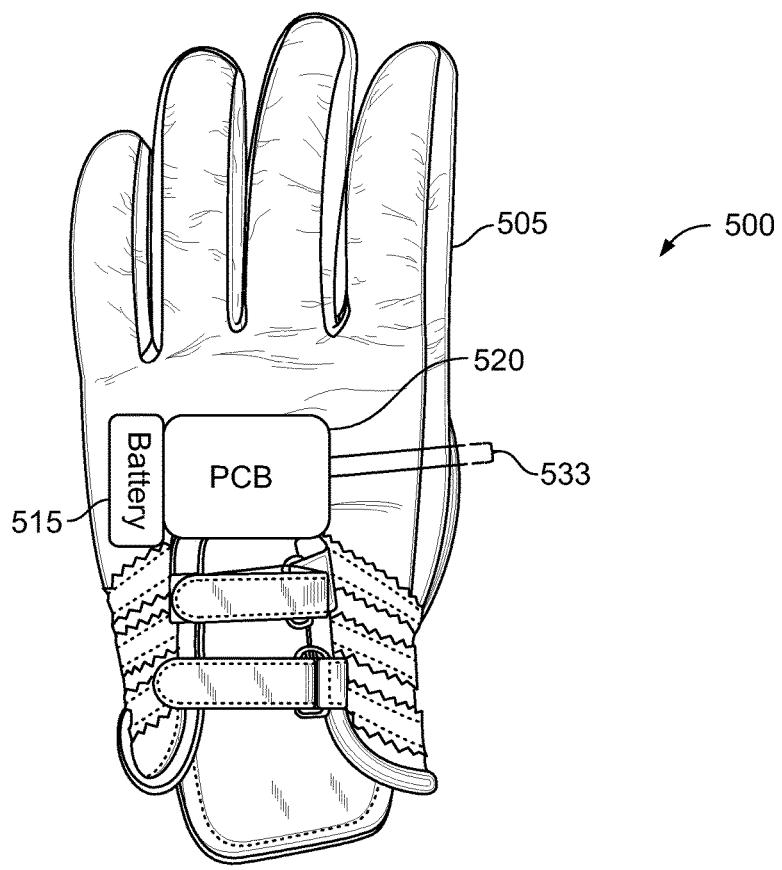
FIG. 5 illustrates an embodiment of the wearable device embodied as a glove.

FIG. 5 illustrates an embodiment of the wearable device 500 embodied as a glove 505. As shown in FIG. 5, the wearable device 500 includes a glove 505, having an attached battery 515, and a Printed Circuit Board (PCB) 520 including all of the remaining components shown in the embodiment of the wearable device of FIG. 3 other than the Force Sensitive Resistors (FSRs). The FSRs are positioned in the palm of the glove and connected to the PCB 520 with two wires 533.

In one embodiment, the wearable device is embedded with a PCB, including a microcontroller, wireless transmission module, memory buffer, on-board MEMS sensors, a microSD connector with a microSD card, biofeedback mechanisms, connectors for external sensors (including Force Sensitive Resistors or load sensors), a voltage regulator, and a power source. In one specific embodiment, a pair of gloves are embedded with a PCB attached to the back of the glove using an adhesive material, such that the PCB is located on the back of the user's palm, below the fingers, centered on the back of the palm as shown. Wires running around the side of the hand connect to Force Sensitive Resistor elements attached to the palm of the glove. Also attached to the back of the glove is a housing with the PCB and the rechargeable battery.

The Printed Circuit Board (PCB) is capable of sensor data collection and wireless data transmission, and includes sensors including force, acceleration, gyroscope and GPS sensors, capable of accurately measuring and securely transmitting real-time wheelchair propulsion technique data to a user mobile device such as a mobile phone, computer, smart watch, or tablet device.

Sensors embedded in the wearable device provides access to measuring various wheelchair propulsion parameters without impairing the hand mobility or comfort of the user. The wearable device automatically collects, processes, locally stores the data in an on-board storage unit (such as a microSD card), and transmits the locally stored data wirelessly to a separate device. Reports of propulsion parameter summaries obtained by the wearable device may be displayed in a separate medium (pc, tablet or phone) and may be used to continuously analyze the deviation from the user's preferred propulsion technique, increasing the ability to detect the onset of potential injuries.

In one embodiment, the battery may be a rechargeable 110 mAh 3.3 volt Polymer Lithium Ion Battery and it may be located on the back of the glove along with the PCB. It may be held inside an ABS plastic enclosure, which is attached to the glove with adhesive material. The battery is attached to the PCB using a JST-XH connector. Ultra low power consumption is achieved through the use of low-power peripherals combined with a power-saving system as further described below.

Figure 6:
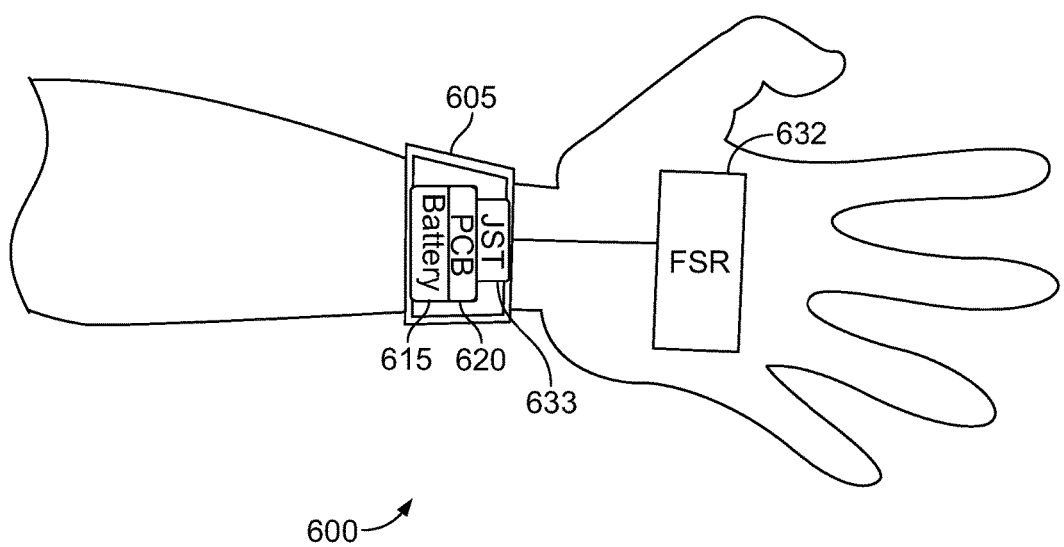
FIG. 6 illustrates an alternate embodiment of the wearable device embodied as a wristband having a connection to receive readings from an external Force Sensing Resistor (FSR).

FIG. 6 illustrates an alternate embodiment of the wearable device 600 embodied as a wristband 605 having a connection to receive readings from an external Force Sensing Resistor (FSR). As shown in FIG. 6, the wearable device 600 includes a wristband 605, having an attached battery 615, and a Printed Circuit Board (PCB) 620 including all of the remaining components shown in the embodiment of the wearable device of FIG. 3 other than the Force Sensitive Resistors (FSRs). The FSRs 632 are positioned in the palm of the user and connected to the PCB 620 using a data connection such as a JST-XH connector 633 to attach and detach the FSR 632. The FSR 632 may also be positioned attached to or embedded in a glove or may be held in or attached to the hand of the user.

With regard to the positioning of the FSRs in one or more of the embodiments herein, FSRs may be attached to the palm of the glove with an adhesive material or may be tailored or stitched on to desired location in order to measure and detect the force applied by the user's hand onto the wheel of the wheelchair. In one embodiment, the sensors may be stitched on to the inner surface of the glove that sits on the user's palm region. In this embodiment, the sensor may not be visible from the exterior of the glove. The FSRs are easily attached and detached from the PCB using a JST-XH series of connectors, allowing the PCB to be located at various locations.

In one embodiment, the PCB is located on the back of the glove as seen in FIG. 5. In a separate embodiment, the PCB is located on a wristband, as seen in FIG. 6. The leads of the FSR may be directly soldered onto the PCB.

The sensor placement on the glove is customizable in multiple ways. Below are various embodiments for the positioning of the FSR. One embodiment of the includes a pair of gloves embedded with one force-sensitive resistor with a sensing area of 1.5"×1.5". This force-sensitive resistor is located on the palm, beneath the fingers such that it is positioned directly above the volar palm of the user when the glove is worn. In a separate embodiment, five circular diameter FSR's (whose diameter may be between 0.2" to 1.5" diameter) are attached to the glove directly beneath the fingers such that each FSR is located directly above ametacarpal head located on the user's hand. In yet another embodiment, up to fourteen small 0.6" circular FSRs are mounted on the front of the glove (inner surface of the glove which is in contact with the palm when the glove is worn), each located in a different location, corresponding to the following regions of the hand:

1. Palm below the second, third, fourth and fifth fingers
2. Palm below the thumb
3. Volar palm
4. Heel of the hand
5. First metacarpal head
6. Second metacarpal head
7. Third metacarpal head
8. Fourth metacarpal head
9. Fifth metacarpal head
10. First distal phalanx
11. Second distal phalanx
12. Third distal phalanx
13. Fourth distal phalanx
14. Fifth distal phalanx In one embodiment, the motion of the hand is measured by a MEMS accelerometer and gyroscope designed for low power consumption. In one embodiment, an Analog Devices ADXL377 triple axis accelerometer is integrated into the PCB in order to measure hand motion acceleration parameters, which, in one embodiment, is embedded onto the rear of the glove, located above the center of the opisthenar area of the user's hand. In a separate embodiment, the MEMS accelerometer and gyroscope is mounted onto a PCB, which is located on a wristband, worn on the wrist by the user. In this embodiment, the force sensors (attached to the glove) connect to the PCB using JST-XH connectors. Both embodiments mentioned above may additionally support multiple types and combinations of accelerometers and gyroscopes. For example, an exemplary embodiment of the present invention utilizes a Bosch BNO055 Intelligent 9-Axis sensor, in replacement of the ADXL377 device. In an additional embodiment, an InvenSense MPU-6000 motion-processing unit is used to measure gyroscopic and accelerometer data. In yet another embodiment, a MPU-6050 unit is used in both methods described above, located on either the opisthenar area of the hand or on the wrist.

A separate embodiment utilizes a MEMS gyroscope and accelerometer that are mounted on the user's shoulder using an elastic band worn directly on the shoulder. The sensors are coupled with JST-XH connectors, which have wires running down the length of the arm are used to connect the MEMS sensors to the PCB.

In one embodiment, third party Bluetooth devices are integrated into this system using a Bluetooth 4.0 communication protocol. For example, one embodiment of the invention uses a GoSafe TPMS 500BT Bluetooth air pressure-monitoring device to measure the tire pressure of the wheelchair. The air pressure data may then be relayed through the Bluetooth system to the User mobile device and used by the user motion dynamics analysis system.

FIG. 7 illustrates an embodiment of the user mobile device 720. As shown in FIG. 7 the user mobile device 710 includes a Bluetooth transceiver 710, a clock 730, a user motion dynamics analysis system 740 including a processor 742 and a memory 744, a Graphical User Interface (GUI) 750, and a cloud communication system 760.

In operation, sensor data is received from the wearable device at the Bluetooth transceiver 710 and alert data is transmitted to the wearable device using to Bluetooth transceiver 710. The Bluetooth transceiver 710 communicates with the processor 742 of the user motion dynamics analysis system 740 which performs the actual analysis of the user/sensor data as described herein. Also, as the processor 742 receives the sensor data it retrieves a timestamp from the clock 730, associates the timestamp with the sensor data, and saves the sensor data and associated timestamp in the memory 744.

The GUI 750 may be used to receive input commands or data from the user, for example entering additional user data to be received by the processor 742 and stored in the memory 744 or for receiving a command to retrieve specific sensor readings from the memory 744 and display them on the GUI 750.

Additionally, as further described below, the cloud communication system 760 may be used to communicated between the user motion dynamics analysis system 740 and a remote cloud server.

In embodiments where data transfer from the wearable device to the user's mobile phone, tablet, smart-watch, computer, or digital display is desired, device and sensor readings along with biometric analytic data are accessible to through the user motion dynamics analysis system which may include a standalone software application. This application may be written in a programming language conforming to the operating system of the peripheral display device or generically through, such as for display through a browser.

The user motion dynamics analysis system receives the sensor data, saves the data with timestamps in order to track data for continuous monitoring and viewing of past history, as well as displays various parameters. This includes summary data such as the average peak force as measured by the wearable device over a specified period of time.

All sensor data is saved to local memory on the user's mobile phone, tablet, or computer in order to allow for long-term analysis of propulsion technique trends. Additionally, all sensor data is saved directly to a microSD card, located on the PCB in a SMD microSD card connector. In one embodiment, the microSD card connector located on the PCB is a Molex 503182 Memory Card Connector. By saving all data over an extended period of time, the user motion dynamics analysis system has the ability to continuously monitor how much the propulsion parameters are changing per unit of time, as well as calculate the magnitude of the changes. The user motion dynamics analysis system additionally allows for the option to upload the gathered data onto the cloud database engine, providing a system for sharing data with a third party. Visualization of desired propulsion parameters is available through the GUI in the form of charts, lists, and graphs. At any point, the user has the option to permanently delete all personal data from the memory and/or cloud server using the user motion dynamics analysis system.

While a user is propelling his/her wheelchair, sensor data is collected and automatically sent wirelessly to the user motion dynamics analysis system on the user's mobile device, tablet, or home computer. This transmission may be achieved using various transmission protocols, including but not limited to Bluetooth, Wifi, NFC, RFID, text message, IEEE 802.11, IrDA, GSM, GPRS, LTE, EDGE, and PCI. Data transmission from the wearable device is achieved using a wireless data transmission protocol. In one embodiment, this is achieved using an nRF8001 low-power Bluetooth IC. Other embodiments utilize an on-chip Bluetooth 4.0 transmitter implemented in various SoC processors. One embodiment uses the on-chip Bluetooth 4.0 transmitter of the Nordic nRF51422 SoC. Other embodiments use the Nordic nRF51822 SoC. Yet another embodiment uses the Nordic nFR52832SoC. Wifi transmission may be used in a specific embodiment instead of Bluetooth transmission. An embodiment of this type uses an ESP8266 WiFi Module SoC as the main processor and wireless transmission module.

FIG. 8 illustrates the data process flow 800 of the wearable user motion dynamics analysis system 200 of FIG. 2. As shown in FIG. 8 and described herein, the wearable device 810 detects, records, and transmits sensor data to the user mobile device 820 for analysis by the user motion dynamics analysis system. The user motion dynamics analysis system receives the sensor data metrics from the wearable device and retrieves from memory wheelchair parameters that were previously input and/or stored by the user and/or a care provider as well as user specific information for risk evaluation that was previously input and/or stored by the user and/or a care provider, both of which are discussed further below.

The user motion dynamics analysis system then computes a shoulder usage summary and injury risk either at the user device or transmits the data to a cloud server for analysis there. The resulting metrics and/or shoulder injury risk information calculated by the user motion dynamics analysis system may then be displayed for the user, for example at the GUI. Additionally, the user motion dynamics analysis system may send alert data to the wearable device over the bio-feedback alert system.

Figure 9:
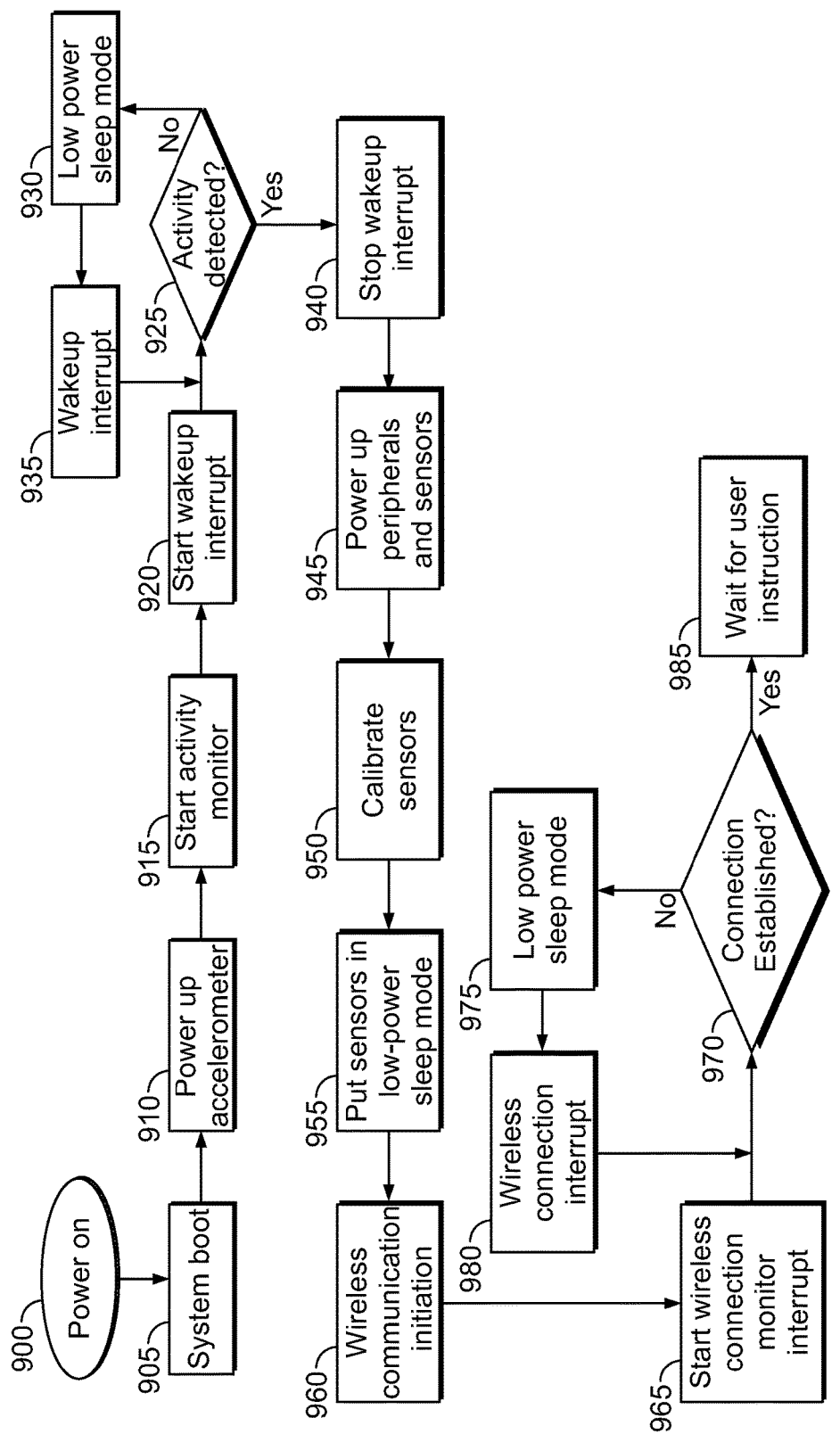
FIG. 9 illustrates a flowchart of a low power usage method for the wearable device.

FIG. 9 illustrates a flowchart 900 of a low power usage method for the wearable device. First, at step 900, power is supplied to the wearable device. Next, at step 905, the sensor system on the wearable device boots up. Then, at step 910, the accelerometer is powered up. Next, at step 915, the activity monitor is started. At step 920, a start wakeup interrupt is triggered and the process proceeds to step 925. At step 925, if no activity is detected at the accelerometer, then the process proceeds to step 930 and the wearable device enters a low power sleep mode. At step 935, the wakeup interrupt is completed and the process proceeds back to step 925 to await the detection of future activity at the accelerometer.

At some point in the future, activity is detected at the accelerometer, so the flowchart proceeds to step 940 and the wakeup interrupt is stopped. The process then proceeds to step 945 and the wearable device's peripherals and sensors are powered up. At step 950, the sensors are calibrated. Next, at step 955, the sensors are places into a low-power sleep mode. At step 960, wireless communication is initiated. Then, at step 965, a wireless connection monitor interrupt is started. The process then proceeds to step 970 where it is determined whether a wireless connection has been established. If the wireless connection has not been established, then the process proceeds to step 975 and the wearable device enters a low power sleep mode and the wireless connection interrupt completes at step 980. The process then proceeds to step 970 and awaits the establishment of a wireless connection. Conversely, if a wireless connection is established at step 970, then the process proceeds to step 985 and the wearable device waits for user instruction.

Figure 10:
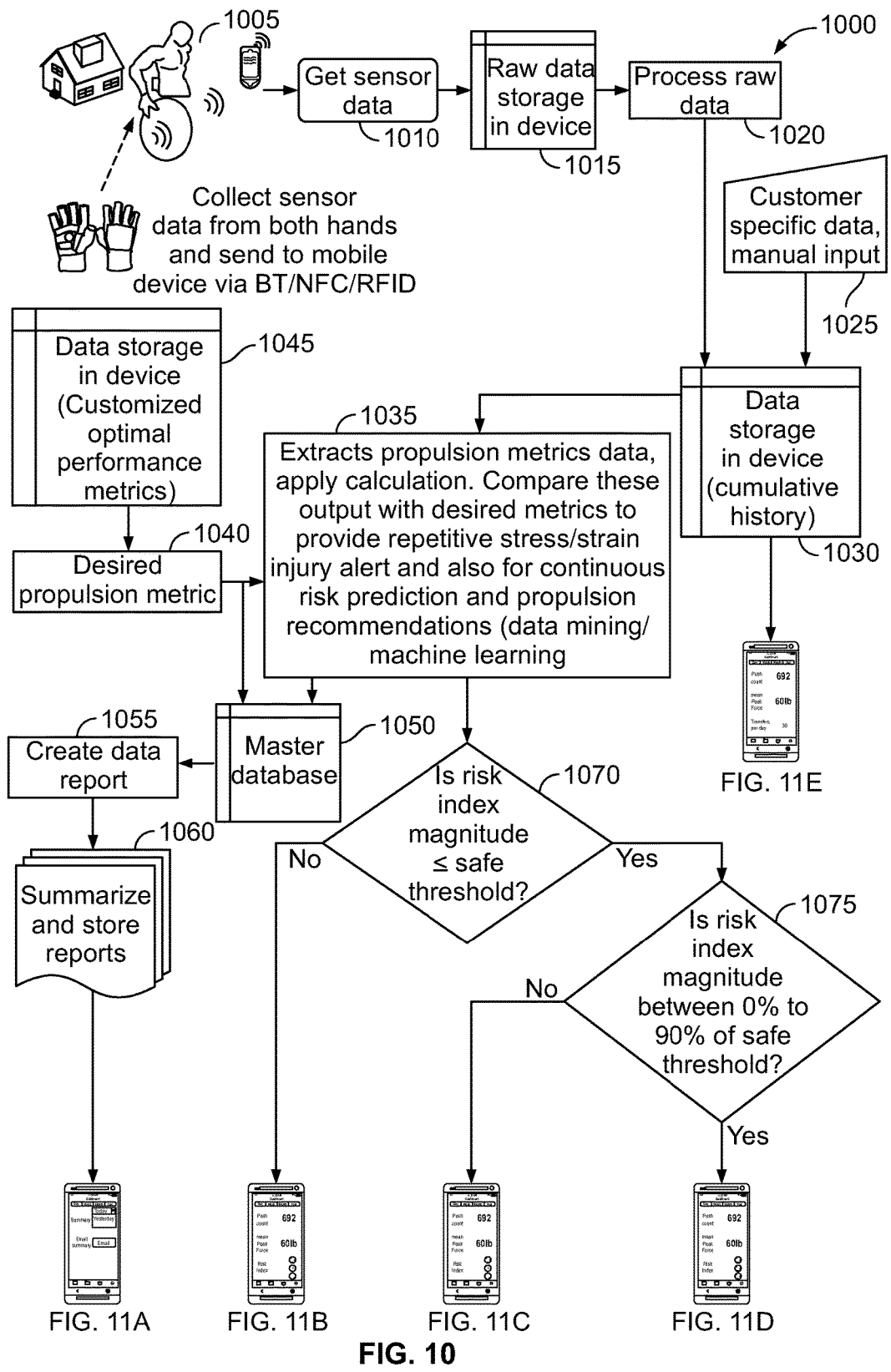
FIG. 10 illustrates the data flow of the calculation of the injury risk score and biofeedback according to an embodiment of the present invention.

FIG. 10 illustrates the data flow 1000 of the calculation of the injury risk score and biofeedback according to an embodiment of the present invention. As shown in FIG. 10, at step 1005, the sensor data is collected from both hands of the wearable device and sent to the mobile device with the corresponding clock time (time stamps). At step 1010 the sensor data is received at the mobile device. At step 1015, the raw data is stored at the mobile device. At step 1020, the raw data is processed by associating a clock time with the type of wheelchair propulsion data activity. At step 1025, user/customer specific data may be input to the mobile device, or may be retrieved from memory if previously stored. At step 1030, all data is stored in the device as a cumulative history for the user.

At step 1035, the user motion dynamics analysis system retrieved data that was previously stored in the device as customized desired performance metrics in step 10454 as well as the desired performance metrics at step 1040. The user motion dynamics analysis system extracts the propulsion metrics data, applies the calculations described herein and compares with desired metrics to provide the repetitive strain injury alert when needed as well as the propulsion metrics and risk prediction. The output is stored in the master database at step 1050.

At some point, a user may desire the creation of a data report, in which case the flowchart proceeds to step 1055 wherein the data report is created. Next, at step 1060, the reports are summarized and stored. Finally, control passes to the report display interface as shown in FIG. 11A.

The report display interface of FIG. 11A allows a user to select a day for which to receive a data report and an email button to initiate the e-mail transmission of the report to a previously stored e-mail address of the user.

Returning to FIG. 10, if the user motion dynamics analysis system determines the risk index is not less than or equal to a safe threshold at step 1070, then the flowchart proceeds to display the data and a risk index warning as shown in FIG. 11B. That is, the display shows the push count in the last 24 hours, the mean peak force, and a risk index. As shown in FIG. 11B, the risk index is displayed similar to a traffic stoplight with the top light being red, the middle being yellow and the bottom being green. In FIG. 11B, it is determined that the risk index is above a safe threshold, so the top, red, light is lit and the other lights are shown in gray.

Alternatively, returning to step 1070, if the process determines that the risk index is less than a safe threshold, the process proceeds to step 1075 and determines whether the risk index magnitude is between 0-90% of the safe threshold. If the risk index magnitude is between 0-90% of the safe threshold, then the process proceeds to display the screen shown in FIG. 11D, which displays the push count, and mean peak force, as well as the bottom, green light, while the other lights are shown in gray.

If the risk index magnitude is between 90-100% of the safe threshold, then the process proceeds to display the screen shown in FIG. 11C, which displays the push count, and mean peak force, as well as the middle, yellow light, while the other lights are shown in gray.

Finally, if actuated by the user, the device may cause to display the screen shown in FIG. 11E, which retrieves from the cumulative history the average number of transfers (moving into or out of the wheelchair) per day. The average number of transfers may be important injury-predicting information because the users entire bodyweight may have to be positioned on their wrists and shoulders during the transfer.

In one embodiment, the flow of sensor information in this system begins with the wearable device, where the data is acquired from the sensors. The data then transfers to a mobile device, computer, or tablet, and finally, if the user desires cloud storage, transmits onto a cloud database engine service for long-term storage. Access to this data is available to user-approved third parties, which include a healthcare provider, trainer, or coach, in order to receive recommendations and training material for improving the propulsion technique. All data that is transmitted through this system may be compressed and encrypted using HTTPS and JSON protocols. A cloud service provider hosting a Platform as a Service (PaaS) is used to store and share data derived from raw sensor data, information derived from the risk-analysis equation, patient data, and healthcare-provided training materials. In one embodiment, the cloud database engine service is the Google App Engine. In yet another embodiment, third party cloud services such as Amazon AWS services are used for the cloud storage functionality. All information that is stored on the cloud database may be secured with encryption keys in order to maintain patient information security and privacy. In a specific embodiment, AES 256-bit encryption is used for this specific component.

The user motion dynamics analysis system provides biofeedback to users on shoulder activity and estimation of shoulder injury risk due to repetitive application of force while propelling their wheelchair. Two of the various possible versions of the user motion dynamics analysis systems include; (1) a stand-alone version and (2) a cloud-integrated version as discussed herein.

Figure 12:
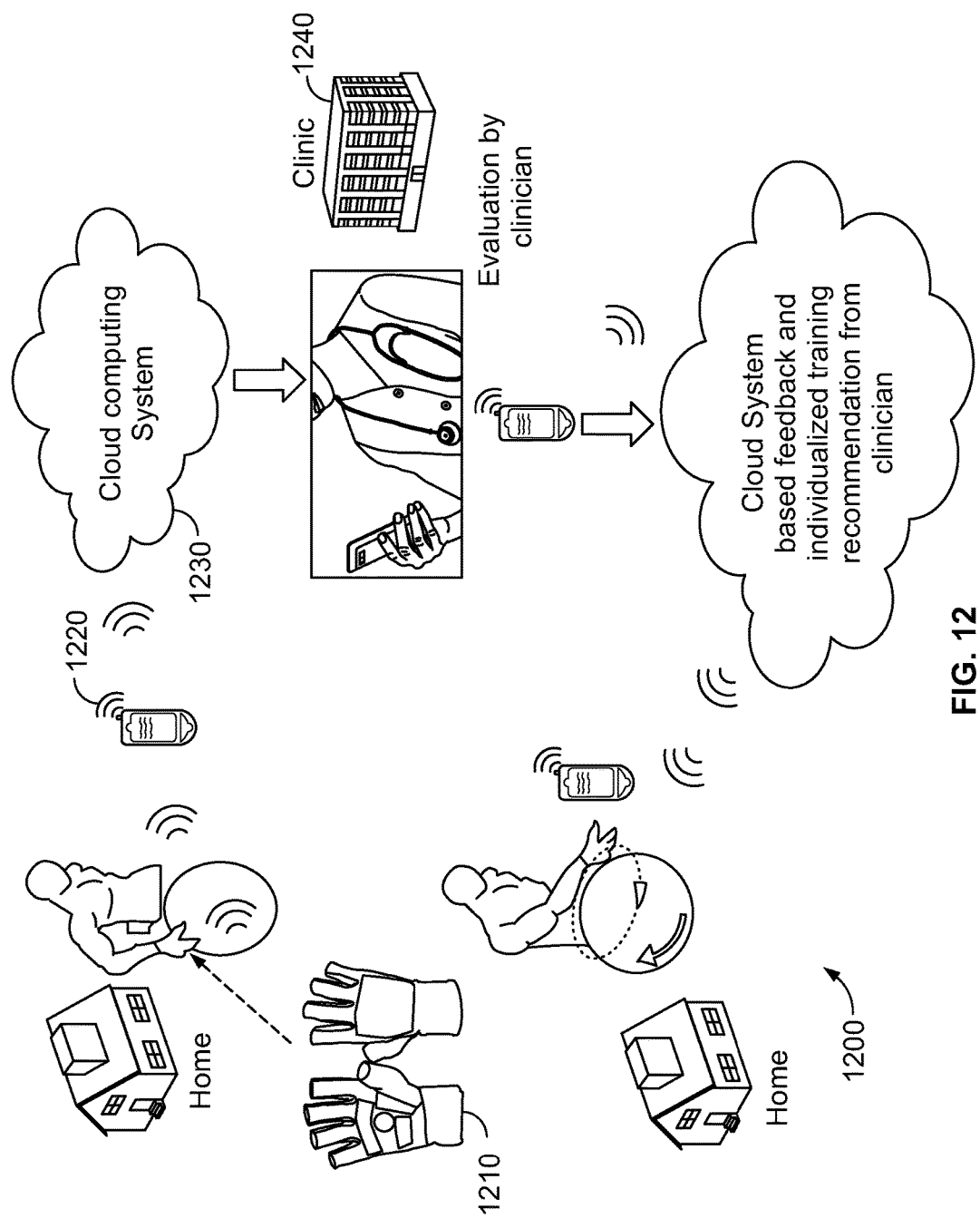
FIG. 12 illustrates a cloud-integrated version according to an embodiment of the present invention.
Figure 13:
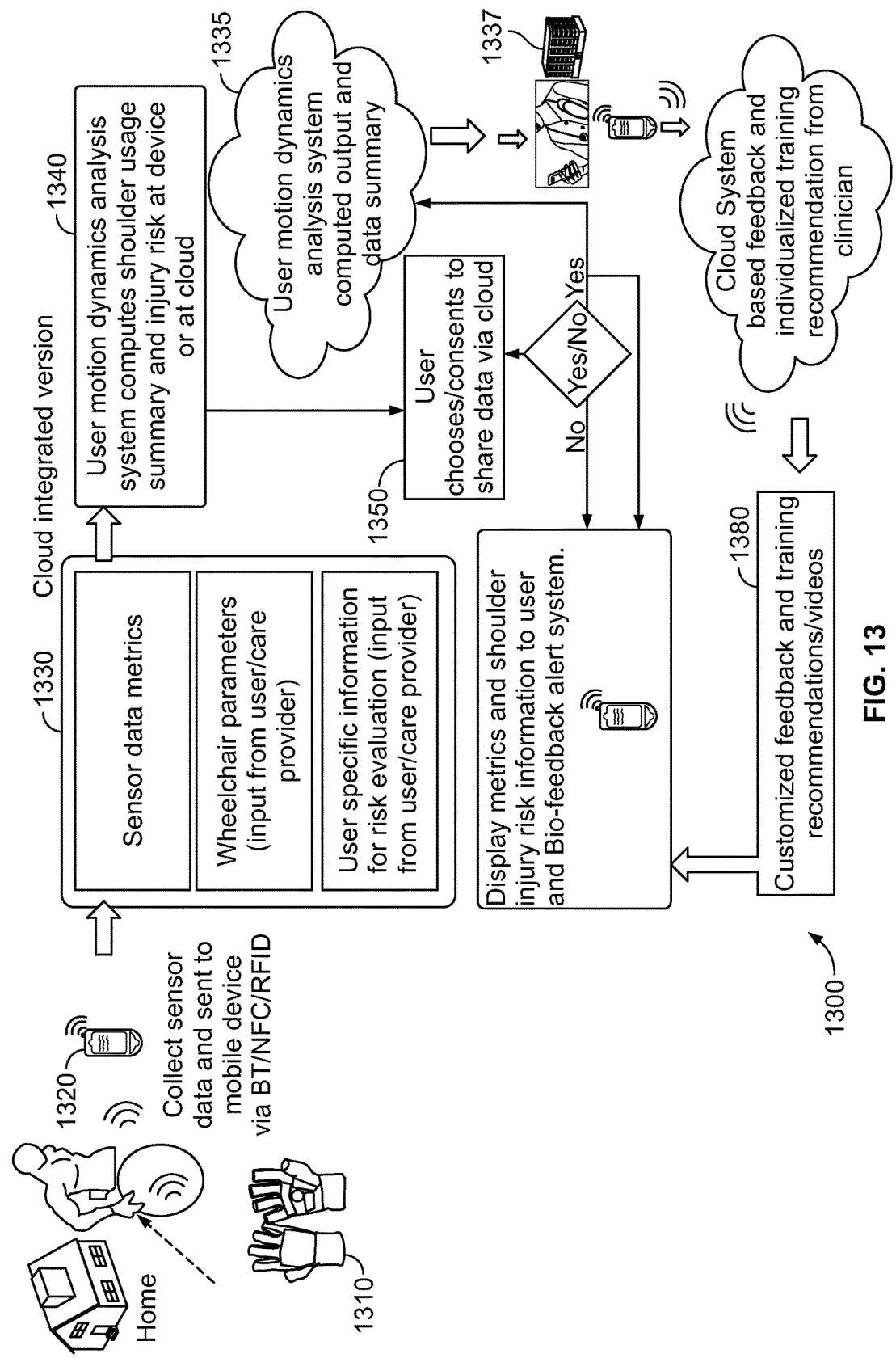
FIG. 13 illustrates the data flow of a cloud-integrated version of the wearable user motion analysis.

FIGS. 12 and 13 illustrate a cloud-integrated version according to an embodiment of the present invention.

As shown in FIG. 12, a wearable device 1210 collects data and transmits it to the user mobile device. The user mobile device then relays the data though a cloud computing system 1230 to a clinic 1240 for evaluation by a clinician. The clinician may observe any recommendations provided by the user motion dynamics analysis system and then provide individualized training recommendations through the cloud system back to the user device for display to the user.

FIG. 13 illustrates the data flow of a cloud-integrated version 1300 of the wearable user motion dynamics analysis system. As shown in FIG. 13, a wearable device 1310 collects data and transmits it to the user mobile device 1320. At 1330 the user motion dynamics analysis system receives the sensor data metrics from the wearable device and retrieves from memory wheelchair parameters that were previously input and/or stored by the user and/or a care provider as well as user specific information for risk evaluation that was previously input and/or stored by the user and/or a care provider, both of which are discussed further below.

At 1340, the user motion dynamics analysis system then computes a shoulder usage summary and injury risk either at the user device or transmits the data to a cloud server for analysis there.

At 1350, the user determined whether the user will allow the data to be transmitted to the clinic using the cloud. When the user chooses not to share the data, the process flow proceeds to 1360 and the resulting metrics and/or shoulder injury risk information calculated by the user motion dynamics analysis system may then be displayed for the user, for example at the GUI. Additionally, the user motion dynamics analysis system may send alert data to the wearable device over the bio-feedback alert system.

Conversely, when the user chooses to share the data, the user mobile device then relays the data though a cloud computing system 1335 to a clinic 1337 for evaluation by a clinician. The clinician may observe any recommendations provided by the user motion dynamics analysis system and then provide individualized training recommendations through the cloud system back to the user device for display to the user at 1380.

The user motion dynamics analysis system integrates user specific qualitative and quantitative measurement from different sources to display the wheelchair propulsion summary and assessment of shoulder injury risk due to the repetitive propulsion of a wheelchair to the user using their mobile device, home computer, or tablet. The user motion dynamics analysis system also activates a bio-feedback method to alert the user if their wheelchair propulsion biomechanical characteristics deviates from the safe zone. The cloud-integrated version of the current invention provides a mechanism for the user to continuously monitor day-to-day performance, share/receive videos for training/therapy and feedback for injury prevention from caregivers through the cloud, serving as an on-the-go technology.

A biofeedback system activates if the risk analysis exceeds a reasonable level, determined individually for each user from a "baseline" level, which is measured after an initial session of proper wheelchair propulsion technique training. This baseline value is updated based on continual evaluation, for example by using a propulsion training at regular intervals to continuously monitor wheelchair propulsion form and performance. The results of the propulsion training may be used to update the baseline.

Sensor data collected during this initial training session is saved as the user's specific "baseline" allowing for the monitoring of deviation from this individually customized "baseline". If at any point the propulsion parameters of the user have shown deviation from the established desired level greater than 10% percent, the system activates the biofeedback system in order to alert the user to make him/her aware of the risk situation. The threshold value (e.g. 10%) is customizable based on needs. In one embodiment, this system includes a vibrating element located on the PCB. The intensity of the vibration increases in proportion to the amount of deviation from the baseline level. In another embodiment, an audio device attached to the PCB is used as the biofeedback mechanism. The audio device activates, producing a unique signature beeping tone, in order to alert the user about the current level of risk of injury. The volume of the tone increases with proportion to the deviation from the baseline level. In a different kind of embodiment, the user motion dynamics analysis system automatically triggers and leaves an automated voice message/email notification to the user's mobile device in order to make the user aware of the situation.

For each user, the user motion dynamics analysis system combines data from sensors and from sources other than sensors to custom track their performance and assess risk of shoulder injury over time.

In an embodiment described herein, there are several main sensor parameters that are used in the user motion dynamics analysis system to monitor wheelchair propulsion. These parameters are extracted from the raw data collected from the sensors attached to the glove.

They are, (1) peak forces at palm while pushing the wheelchair, which is extracted from force sensors data by picking the maximum cumulative summed value during each push. The force values from each sensor maximum value are picked based on three conditions; first, that force value is higher than a certain threshold; second, that the wrist acceleration and orientation in X direction changed (e.g. only then they are pushing or else they are just moving the hand without pushing) and; third that the acceleration of the wheelchair increases (e.g. the wheelchair moves). This is computed from the inertial sensor data attached to the wheelchair or a GPS module attached to the wearable sensor.

The second parameter is (2) acceleration patterns at the wrist during wheelchair propulsion/recovery. This is extracted from acceleration sensor data using the zero crossings signature of the acceleration signals from hand and the X, Y, and Z direction acceleration amplitude signature.

The third parameter is (3) the number of pushes. This is extracted from force sensor data signature by counting the number of maximum values that occurs over a given time (e.g. the count of the maximum value is equal to the number of pushes), The fourth parameter is (4) mean speed. This is a computed hand velocity from acceleration sensor data and averaged over the pushes to find mean speed. Alternatively, this may also be computed from the acceleration signal of the inertial sensor attached to the wheelchair.

The fifth parameter is (5) contact angle of push. This may be extracted from acceleration sensor data by computing the duration of the linear portion of the acceleration curve during push phase and combining it with the mean push velocity information to calculate an angular measure (e.g. contact angle) during each push)

The sixth parameter is (6) push time. This may be extracted from the linear portion of the acceleration signal during the push phase. The contact time per push may be computed this way and then may be summed over the entire period to compute the total push time and average push time. The push time value is considered valid for based on three conditions; first, that force value is higher than a certain threshold; second, that the wrist acceleration and orientation in X direction changed (e.g. only then they are pushing or else they are just moving the hand without pushing)) and; third, that the acceleration of the wheelchair increases (e.g. the wheelchair moves). This is computed from the inertial sensor data attached to the wheelchair.

The seventh parameter is (7) push distance. This is computed using the mean speed per push and number of pushes.

The eighth parameter is (8) wrist flexion/extension angles. This may be extracted from the gyroscope sensor data from hardware.

The ninth parameter is (9) number of bouts. This is based on acceleration sensor activity e.g. rest and active periods. Push activity packed between any two 1 minute rest period will be counted as a bout.

The tenth parameter is (10) number of breaks to initiate a stop and number of start-up to initiate a push (extracted from the peak jerk pattern and the number of bouts).

The eleventh parameter is (11) momentary impact/cumulative impact endured by the arm joints during push and recovery. This is computed as peak value/area under the acceleration or jerk curve for every push/recovery event.

The twelfth parameter is (12) frequency of repetitions. This is the number of peak force events for each bout computed over the entire period.

The thirteenth parameter is (13) active time on a particular time interval/day-to-day basis. This is computed from the total push time and bouts.

The fourteenth parameter is (14) muscle activity (EMG) which is extracted from the EMG sensor data.

The fifteenth parameter is (15) Grip strength which is extracted from the force sensor data by taking grip strength measurements devices such as hand grip dynamometer.

The sixteenth parameter is (16) Push time to rest time ratio. This is determined from push time and activity time. A variation of this as a ratio between push time to recovery time during wheelchair propulsion.

The seventeenth parameter is (17) Peak force at palm during transfer activity. This is extracted and identified using the force sensor magnitude (threshold if the peak force is greater than ~1.5 times the usual mean value of peak force during pushing) and acceleration sensor value such that the acceleration in X direction is near zero, acceleration in Z and Y direction changes.

The eighteenth parameter is (18) Trunk acceleration pattern. This is a motion/acceleration sensor attached on the trunk (torso) to measure motion smoothness during transfer to quantify the quality of transfer. The trunk acceleration pattern may also be extracted during normal propulsion.

The nineteenth parameter is (19) number of transfers. This is the count of number of events of (18) from the torso motion/acceleration sensor signature. Transfers are performed when the wheelchair is stationary. The data from various sensors (tri-axial accelerometer and GPS will be used to identify this).

The twentieth parameter is (20) wheelchair pushed in level or incline. This is extracted from inertia sensor data signature which is attached to the wheelchair, The twenty-first parameter is (21) Tire pressure which is obtained wirelessly using third party Bluetooth tire pressure monitoring device attached to the tire.

The twenty-second parameter is (22) heart rate which is obtained using data from third party device whose data may be integrated with the sensor data from PCB and/or using the user motions dynamics analysis system.

The twenty-third parameter is (23) using computational techniques to extract the propulsion parameter information for elbow and shoulder joint from the wrist sensor data (e.g. force, acceleration, orientation, distance) and user specific anthropometry. This may be determined using inverse dynamic models. e.g. compute the shoulder force using inverse dynamics procedures given the force at palm, the arm anthropometric properties and wrist acceleration data.

Other sensors types, may also be integrated into the present invention.

Additionally, the user motion dynamics analysis system may receive data from sources other than sensors including user specific data such as,

(24) user demographics (gender, age, height, weight, BMI etc),

(25) healthcare condition specific to user (for example injury type, time since injury, ability to control specific anatomical upper limb musculature/joint to coordinate wheelchair propulsion (using standard assessment scales as input by the user based on their report from PT), whether congenial pathology or vice versa etc),

(26) user anthropometry,

(27) history of pain/injury/surgery in arm joints (will be collected for a series of ADL activities using standard scales like WUSPI, VAS for upper limb, input from healthcare professional on pain diagnosis etc. These options will be provided in the interface for the users to input the information in collaboration with their healthcare professional. The calculation's accuracy increases when the user includes more of such health information,

(28) wheelchair build (e.g. weight, configuration used, wheelchair type, tire type, etc),

(29) self-perceived quality of independent living and self esteem assessment scores and

(30) other third party sensor based reports that may be incorporated (for example: ultrasound measures/scores, arm joint injury image scores (MRI etc)).

The user motion dynamics analysis system's calculations uses the information extracted by sources belonging to sensor and user specific data, mines the data to extract and display useful health information to users through their mobile device as described herein.

Below are listed a few such categories of information that may be provided by the user motion dynamics analysis system:

(1) Daily activity type and duration monitoring
(2) Transfer activity/performance tracking
(3) Propulsion pattern signature tracking
(4) extract risk assessment scores to help the user track their performance and alert them on potential risky propulsion practices than may lead to injury.

FIGS. 14A and 14B illustrate an example of the calculation of the user demographics specific risk exposure score.

FIG. 15 illustrates an example of the calculation of the user perceived pain exposure score.

FIG. 16 illustrates an example of the calculation of the user perceived quality of life score.

FIGS. 17A to 17D illustrate an example of the calculation of the wheelchair propulsion score.

FIGS. 18A and 18B illustrate an example of the calculation of the transfer score.

The user motion dynamics analysis system customizes to each user's condition, quantifies and displays useful information. The information includes, but is not limited to, the user's day-to-day propulsion activity as a summary, assessment of shoulder injury risk to improve awareness of health, to inform the user when it is desirable to seek preventive healthcare and to help user get access to necessary rehabilitation training resources. One such embodiment which describes the procedure for computing the risk scores with a hypothetical example is listed in the Table 1.

Embodiment 1

At the end of a particular time interval, (ex. after 2 weeks).
User profile: User name: Mike
Table 1 illustrates a sample risk score calculation

TABLE 1

| Variable ensemble count | Calculation inputs parameters | Risk Scores (all scores are in a scale between 0 to 10) |
|---|---|---|
| 1 | Assume body weight = 200 lb; Height = 5 foot 8 inch. (BMI = 30.4) | 8 |
|  | Wheelchair weight = 35 lb; | 6 |
| 2 | Number of Pushes/minute: 30 pushes/minute. | 5 |
| 3 | Average peak resultant force per push/per arm: 25 lbs | 2 |
| 4 | Total push time per day: 60 minute | 3 |
| 5 | Number of bouts during this 60 minutes: 30 (So number of Start + Stop (braking) = 60 and Number of breaking = 30): Impact lading risk score: | 6 |
| 6 | Self perceived pain score | 6 |
| 7 | Risk factor due to improper wheelchair configuration | 7 |
| 8 | Age of Injury (24) | 6 |
| 9 | Gender (male) | 1 |
| 10 | Time since injury (10 years) | 9 |
|  | Average scores | 4.8 |

Using a risk score scale as shown below in Table 2

TABLE 2

| Risk Scores | RSI risk |
|---|---|
| 1-3 (green) | Negligible to low risk |
| 4-6 (yellow) | Medium risk, Watch out |
| 6+ (red) | High risk, Seek help |

If the user's desired risk score was 2 (established initially), and since the current average risk scores is 4.8, which is greater than 10% of the desired set value, the user is at a higher risk (red signal glows in the app) and bio-feedback alerts are triggered. The bio-feedback alerts the user of the situation by multiple modes. The user may share this data with his healthcare provider to seek help to reduce the risk score. The healthcare provider may send recommendations to the user through the cloud service/text/voice/call/skype as recommend suggestion for physical rehabilitation training to relax the muscles, suggesting more rest period between pushes etc.

Embodiment 2

At the end of a particular time interval, (ex. after 2 months).
User profile: User name: Ana
Table 3 illustrates another exemplary risk score calculation.

TABLE 3

| Variable ensemble count | Calculation inputs parameters | Risk Scores (all scores are in a scale between 0 to 10) |
| --- | --- | --- |
| 1 | Assume body weight = 100 lb; Height = 5 foot 8 inch. (BMI = 21.4) | 6 |
|   | Wheelchair weight = 30 lb; | 6 |
| 2 | Number of Pushes/minute: 50 pushes/minute. | 7 |
| 3 | Average peak resultant force per push/per arm: 18 lbs | 1 |
| 4 | Total push time per day: 120 minute | 6 |
| 5 | Number of bouts during this 120 minutes: 60 (number of Start + Stop (braking) = 120 and Number of breaking = 60): Impact lading risk score: | 8 |
| 6 | Self perceived pain score | 2 |
| 7 | Risk factor due to improper wheelchair configuration | 5 |
| 8 | Age of Injury (8) | 3 |
| 9 | Gender (female) | 2 |
| 10 | Time since injury (21 years) | 7 |
| 11 | Possibility of injury risk based off of medical reports (Ultrasound, X ray, MRI etc) | 5 |
|   | Average scores | 5.5 |

Using the same risk scale shown above in Table 2, Ana will be placed at a medium risk zone.

Embodiment 3

At the end of a particular time interval, (ex. after 2 months).

User profile: User name: James

Table 4 illustrates another exemplary risk score calculation.

TABLE 4

| Variable ensemble count | Calculation inputs parameters | Risk Scores (all scores are in a scale between 0 to 10) |
| --- | --- | --- |
| 1 | Assume body weight = 300 lb; Height = 6 foot. | 8 |
|   | Wheelchair weight = 35 lb; | 7 |
| 2 | Number of Pushes/minute: 30 pushes/minute. | 5 |
| 3 | Average peak resultant force per push/per arm: 40 lbs | 7 |
| 4 | Total push time per day: 90 minute | 6 |
| 5 | Number of bouts during this 90 minutes: 30 | 6 |
| 6 | Self perceived pain score | 8 |
| 7 | Risk factor due to improper wheelchair configuration | 9 |
| 8 | Age of Injury (34) | 8 |
| 9 | Gender (male) | 1 |
| 10 | Time since injury (16 years) | 7 |
| 11 | Possibility of injury risk due to propulsion based off of medical reports on shoulder (Ultrasound, X ray, MRI etc) | 6 |
| 12 | Self rated dissatisfaction with quality of living | 7 |
|   | Average scores | 7.1 |

Using the same risk scale shown above in Table 2, James will be placed at a medium risk zone.

In another embodiment the risk score may be computed as weighted average and/or accompanied with a weighted look up table to arrive at the final risk score.

Embodiment 4

At the end of a particular time interval, (ex. after 2 months).

User profile: User name: Aba

Table 5 illustrates another exemplary risk score calculation.

TABLE 5

| Variable ensemble count | Calculation inputs parameters | Risk Scores (all scores are in a scale between 0 to 10) |
| --- | --- | --- |
| 1 | Assume body weight = 100 lb; Height = 5 foot 8 inch. (BMI = 21.4) | 6 |
|   | Wheelchair weight = 30 lb; | 6 |
| 2 | Number of Pushes/minute: 50 pushes/minute. | 7 |
| 3 | Average peak resultant force per push/per arm: 18 lbs | 1 |
| 4 | Total push time per day: 120 minute | 6 |
| 5 | Number of bouts during this 120 minutes: 60 (number of Start + Stop (breaking) = 120 and Number of breaking = 60): Impact lading risk score: | 8 |
| 6 | Self perceived pain score | 2 |
| 7 | Risk factor due to improper wheelchair configuration | 5 |
| 8 | Age of Injury (8) | 3 |
| 9 | Gender (female) | 2 |
| 10 | Time since injury (21 years) | 7 |
| 11 | Possibility of injury risk based off of medical reports (Ultrasound, X ray, MRI etc) | 5 |
| 12 | Contact angle | 5 |
| 13 | Total number of transfers: 18 (Car transfer: 6; Bed transfer: 3; transfer for other activities of daily living: 9) | 6 |
| 14 | Peak Elbow and shoulder forces | 7 |
| 15 | Average resultant forces at wrist, elbow, shoulder | 6 |
| 16 | Proper trunk posture | 4 |
| 17 | Desired tire pressure | 6 |
| 18 | Impacts (Jerk) in arm joints | 7 |
|   | Average scores | 5.7 |

Using the same risk scale shown above in Table 2, Aba will be placed at a medium risk zone.

One or more embodiments of the present invention utilize wirelessly obtained data from a set of sensors modalities embedded in a wearable glove. The wearable device continuously captures users limb motion pattern for activity performed, characteristics of repeated usage of limb for activities of daily living (in-clinic and out-patient (at community) mode), the grip force used repeatedly in different hand orientations, and the duration and location of activities. The sensor data is integrated and fused or combined with other user specific qualitative & quantitative information (physiologic, experience, anthropometry, injury history, wheelchair propulsion parameters (temporal, spatial, and dynamics), wheelchair configuration, health status, activity level and propulsion environment) using a novel calculations to measure and learn user specific pattern of wheelchair propulsion biomechanics and predict the risk of repetitive stress/strain injury to the arm joints. Implementing the novel calculation leads to customized wheelchair propulsion rehabilitation medicine for MWCUs. One or more of the embodiments of the present invention are very novel and unique in that it collects and fuses force, movement and inertia data using during both during push and recovery phase of wheelchair propulsion using the same body worn sensor system.

Continuous monitoring of sensor data allows for analysis and viewing of data at any time using the user's mobile device, computer, tablet, smart watch, TV and other digital display media application through logging of sensor data, both remotely (cloud-based) and locally (local storage).

Reports of propulsion parameter summaries obtained by the wearable device may be displayed in a separate medium (pc, tablet or phone) and may be used to continuously analyze the deviation from the user's preferred propulsion technique, increasing the ability to detect the onset of potential injuries.

The various specific embodiments described herein detail the features and main advantages of the wearable device.

1. A non-invasive wearable device solution allowing for the continuous and wireless collection of multiple modality sensor data.

2. The wheelchair propulsion parameters or assistive device use may be determined using the sensor data from the device.

3. Provides a method for self-monitoring of wheelchair propulsion technique or assistive device use/technique.

4. Healthcare providers may view and analyze wheelchair propulsion technique parameters and wheelchair user activity in order to assess risk of injury due to the repetitive action of propelling the manual wheelchair.

5. A method to securely transmit propulsion parameter data to a third party, including a health-care provider.

6. Wireless features provide a method for remote propulsion-technique/physical rehabilitation training sessions with a third party. This includes a method for customized rehabilitation/training materials recommended by a healthcare provider to be transmitted securely to the user's mobile device.

7. A bio-feedback system to alert the user in real time of impending injury risk due to improper propulsion technique.

8. Detecting deviation from preferred and/or desired propulsion techniques through the automatic analysis of longitudinal data collection and/or continuously collected user data.

9. A customized individuals specific risk-score policy automatically estimates the risk of injury in real time and alerts the user of impending injury.

10. Improves patient-provider communications for better healthcare.

11. Improves the ability for the user to adhere to treatment and rehabilitation regimes.

12. A system for shared decision-making with medical professionals based on best available evidence, provided by sensor data.

13. Incorporates telemetry and remote access in the acquisition, analysis and monitoring of biomedical data.

14. Compatible with tele-health systems.

15. Capable of incorporating third party sensor data into the risk-assessment system and health care reporting system.

16. Wheelchair user activity monitoring in order to detect medical needs and events.

17. Home-use capabilities for providing health care/preventive healthcare to prevent repetitive stress/strain overuse injuries in individuals using assistive device like wheelchair.

18. Used as a diagnostic tool to customize assistive device for user or to help user chose the right assistive device based on the grip force safety.

19. A wearable device that enables a real time, long duration continuous motion capture using sensors of multiple modalities, no limiting to accelerometer, gyroscope, GPS and force sensor data.

While particular elements, embodiments, and applications of the present invention have been shown and described, it is understood that the invention is not limited thereto because modifications may be made by those skilled in the art, particularly in light of the foregoing teaching. It is therefore contemplated by the appended claims to cover such modifications and incorporate those features which come within the spirit and scope of the invention.

The invention claimed is:

1. A wheelchair user strain injury alert system, said system including:
    a wearable device, wherein said device is worn on the hand of a wheelchair user, wherein said wearable device includes:
        one or more force sensing resistors positioned proximal to the palm of the user's hand when said wearable device is worn, wherein said one or more force sensing resistors determine grip force data representing the force of said user gripping said wheelchair; and
        a user feedback system including an alert display; and
    a user motion dynamics analysis system, wherein said user motion dynamics analysis system includes a memory storing a user-specific grip force risk table,
    wherein said user motion dynamics analysis system receives said grip force data and compares said grip force data to said grip force risk table to determine a grip force risk score,
    wherein said user motion dynamics analysis system compares said grip force risk score to a predetermined overall average risk score table and generates alert data when said overall average risk score exceeds a predetermined threshold,
    wherein said user feedback system receives said alert data and displays an alert using said alert display in response to the receipt of said alert data.

2. The system of claim 1 wherein said memory also stores user physical characteristics data representing one or more physical characteristics of said user,
    wherein said user motion dynamics analysis system compares said user physical characteristics data to a predetermined user physical characteristics risk table to determine a user physical characteristic risk score,
    wherein said overall average risk score is determined by averaging said physical characteristic risk score and said grip force risk score.

3. The system of claim 1 further including:
    a gyroscope determining wrist angular movement data representing wrist angular movement of said user,
    wherein said user motion dynamics analysis system receives said wrist angular movement data and compares said wrist angular movement data to a predetermined wrist angular movement risk table to determine a wrist angular movement risk score,
    wherein said overall average risk score is determined by averaging said wrist angular movement risk score and said grip force risk score.

4. The system of claim 1 further including:
an accelerometer determining wrist acceleration data representing the acceleration pattern of said user's wrist during wheelchair use,
wherein said user motion dynamics analysis system receives said wrist acceleration data and compares said wrist acceleration data to a predetermined wrist acceleration risk table to determine a wrist acceleration risk score,
wherein said overall average risk score is determined by averaging said wrist acceleration risk score and said grip force risk score.

5. The system of claim 1 wherein said user motion dynamics analysis system identifies a plurality of peaks in said grip force data, determines a number of grip force peaks occurring in a predetermined time frame, and compares said number of grip force peaks to a predetermined threshold to determine a number of peaks risk score,
wherein said overall average risk score is determined by averaging said number of peaks risk score and said grip force risk score.

6. The system of claim 1 wherein said alert provides sensory feedback to said user.

7. A method for alerting a wheelchair user of an increased risk of a strain injury, said method including:
positioning a wearable device on a hand of a user of a wheelchair wherein said wearable device includes:
one or more force sensing resistors positioned proximal to the palm of the user's hand when said wearable device is worn, wherein said one or more force sensing resistors determine grip force data representing the force of said user gripping said wheelchair; and
a user feedback system including an alert display; and
transmitting said grip force data to a user motion dynamics analysis system, wherein said user motion dynamics analysis system includes a memory storing a user-specific grip force risk table;
determining a grip force risk score, at said user motion dynamics analysis system, by comparing said grip force data with said grip force risk table;
comparing said grip force risk score to a predetermined overall average risk score table;
generating alert data when said overall average risk score exceeds a predetermined threshold; and
receiving said alert data at said user feedback system and displaying an alert using said alert display in response to the receipt of said alert data.

8. The method of claim 7 wherein said memory also stores user physical characteristics data representing one or more physical characteristics of said user,
further including:
determining a user physical characteristic risk score, at said user motion dynamics analysis system, by comparing said user physical characteristics data with a predetermined user physical characteristics risk table;
averaging said user physical characteristic risk score and said grip force risk score and comparing said average to said predetermined overall average risk score table;
generating said alert data when said overall average risk score exceeds a predetermined threshold.

9. The method of claim 7 further including:
positioning a gyroscope on said wearable device;
determining wrist angular movement data representing wrist angular movement of said user using said gyroscope,
wherein said user motion dynamics analysis system receives said wrist angular movement data and compares said wrist angular movement data to a predetermined wrist angular movement risk table to determine a wrist angular movement risk score,
averaging said wrist angular movement risk score and said grip force risk score and comparing said average to said predetermined overall average risk score table; and
generating said alert data when said overall average risk score exceeds a predetermined threshold.

10. The method of claim 7 further including:
positioning an accelerometer on said wearable device;
determining wrist acceleration data representing the acceleration pattern of said user's wrist during wheelchair use using said accelerometer
wherein said user motion dynamics analysis system receives said wrist acceleration data and compares said wrist acceleration data to a predetermined wrist acceleration risk table to determine a wrist acceleration risk score,
averaging said wrist acceleration risk score and said grip force risk score and comparing said average to said predetermined overall average risk score table; and
generating said alert data when said overall average risk score exceeds a predetermined threshold.

11. The method of claim 7 further including:
identifying, at said user motion dynamics analysis system, a plurality of peaks in said grip force data;
determining a number of grip force peaks occurring in a predetermined time frame;
comparing said number of grip force peaks to a predetermined threshold to determine a number of peaks risk score,
averaging said number of peaks risk score and said grip force risk score and comparing said average to said predetermined overall average risk score table; and
generating said alert data when said overall average risk score exceeds a predetermined threshold.

12. The method of claim 7 wherein said alert provides sensory feedback to said user.

* * * * *